US009890384B2

(12) United States Patent
Mueller et al.

(10) Patent No.: US 9,890,384 B2
(45) **Date of Patent: *Feb. 13, 2018**

(54) RECOMBINANT MICROORGANISMS AND USES THEREFOR

(71) Applicant: LanzaTech New Zealand Limited, Auckland (NZ)

(72) Inventors: Alexander Paul Mueller, Auckland (NZ); Michael Koepke, Auckland (NZ); Shilpa Nagaraju, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 600 days.

This patent is subject to a terminal disclaimer.

(21) Appl. No.: 13/914,234

(22) Filed: Jun. 10, 2013

(65) Prior Publication Data

US 2013/0330809 A1 Dec. 12, 2013

Related U.S. Application Data

(60) Provisional application No. 61/657,292, filed on Jun. 8, 2012.

(51) Int. Cl.
*C12N 1/20* (2006.01)
*C12N 9/04* (2006.01)
(Continued)

(52) U.S. Cl.
CPC ............... *C12N 15/74* (2013.01); *C12N 1/20* (2013.01); *C12N 9/0006* (2013.01); *C12N 9/88* (2013.01);
(Continued)

(58) Field of Classification Search
None
See application file for complete search history.

(56) References Cited

U.S. PATENT DOCUMENTS 5,173,429 A 12/1992 Gaddy et al.
5,593,886 A 1/1997 Gaddy et al.
(Continued)

FOREIGN PATENT DOCUMENTS

WO WO02-08438 1/2002
WO 2007130521 A1 11/2007
(Continued)

OTHER PUBLICATIONS

Ui, S et al., Production of L-2,3-butanediol by a new pathway constructed in *Escheria coli*, Lett. Appl. Microbiol., 2004 vol. 39, pp. 533-537.

(Continued)

*Primary Examiner* — Richard Ekstrom
(74) *Attorney, Agent, or Firm* — Andrea Schoen

(57) ABSTRACT

Carboxydotrophic acetogenic microorganisms do not produce MEK and/or 2-butanol. They lack the biosynthesis pathways to make these products. In addition, they produce the intermediate (R,R)-2,3-butanediol whereas the production of MEK and 2-butanol requires production of the intermediate (R,S)-2,3-butanediol. Nonetheless, the production of MEK and/or 2-butanol can be accomplished using recombinant microorganisms adapted to express or overexpress key enzymes in the MEK and/or 2-butanol biosynthesis pathways. Such microorganisms, such as the carboxydotrophic acetogen *Clostridium autoethanogenum*, can ferment substrates comprising CO. The overall scheme involves the production of 2-butanol from (R,S)-2,3-butanediol and the conversion of (R)-acetoin to (S)-2,3-butanediol. These steps are involved in the production of both MEK and 2-butanol. Such fermentation methods offer a means of using carbon monoxide from industrial processes which would otherwise be released into the atmosphere and pollute the environment.

15 Claims, 8 Drawing Sheets

(51) Int. Cl.
*C12N 9/88* (2006.01)
*C12N 15/74* (2006.01)
*C12P 7/16* (2006.01)

(52) U.S. Cl.
CPC ......... *C12P 7/16* (2013.01); *C12Y 101/01004* (2013.01); *C12Y 402/0103* (2013.01); *C12Y 402/01028* (2013.01); *Y02E 50/10* (2013.01)

(56) References Cited

U.S. PATENT DOCUMENTS

| | | | | |
|---|---|---|---|---|
| 6,368,819 | B1 | 4/2002 | Gaddy et al. | |
| 2007/0259410 | A1* | 11/2007 | Donaldson et al. | 435/148 |
| 2007/0292927 | A1 | 12/2007 | Donaldson et al. | |
| 2008/0274522 | A1* | 11/2008 | Bramucci et al. | 435/148 |
| 2009/0203139 | A1* | 8/2009 | Larossa et al. | 435/440 |
| 2010/0086644 | A1* | 4/2010 | Dequin et al. | 426/51 |
| 2010/0112655 | A1* | 5/2010 | Paul | 435/160 |
| 2010/0151543 | A1 | 6/2010 | Reeves | |
| 2011/0124060 | A1* | 5/2011 | Anthony et al. | 435/115 |
| 2011/0229947 | A1 | 9/2011 | Zahn et al. | |

FOREIGN PATENT DOCUMENTS

| | | | |
|---|---|---|---|
| WO | WO2008-028055 | | 3/2008 |
| WO | WO2009-064200 | | 5/2009 |
| WO | 2009151342 | A1 | 12/2009 |
| WO | 2010057022 | A1 | 5/2010 |
| WO | WO 2012-053905 | | 4/2012 |
| WO | WO2012-115527 | | 8/2012 |
| WO | 2014092562 | A1 | 6/2014 |

OTHER PUBLICATIONS

Abrini, J., Naveau, H., & Nyns, E. J. *Clostridium autoethanogenum*, sp. nov., an anaerobic bacterium that produces ethanol from carbon monoxide. Archives of microbiology, 161(4), 345-351(1994).

Collins, M. D., Lawson, P. A., Willems, A., Cordoba, J. J., Fernandez-Garayzabal, J., Garcia, P., Cai, J., et al. The phylogeny of the genus *Clostridium*: proposal of five new genera and eleven new species combinations. International journal of systematic bacteriology, 44(4), 812-26(1994).

Herbert, M., O'Keeffe, T. a., Purdy, D., Elmore, M., & Minton, N. P. Gene transfer into Clostridium difficile CD630 and characterisation of its methylase genes. FEMS Microbiology Letters, 229(1), 103-110(2003).

Jennert, K. C., Tardif, C., Young, D. I., & Young, M. Gene transfer to Clostridium cellulolyticum ATCC 35319. Microbiology (Reading, England), 146 Pt 12, 3071-80(2000).

Kita, A., Iwasaki, Y., Sakai, S., Okuto, S., Takaoka, K., Suzuki, T., Yano, S., et al. Development of genetic transformation and heterologous expression system in carboxydotrophic thermophilic acetogen Moorella thermoacetica. Journal of Bioscience and Bioengineering, vol. 115 (4) pp. 347-352 (2013).

Köpke, M., Held, C., Hujer, S., Liesegang, H., Wiezer, A., Wollherr, A., Ehrenreich, A., et al. Clostridium ljungdahlii representa a microbial production platform based on syngas. Proceedings of the National Academy of Sciences of the United States of America, 107(29)(2010).

Köpke, M., Mihalcea, C., Liew, F., Tizard, J. H., Ali, M. S., Conolly, J. J., Al-Sinawi, B., et al. 2,3-Butanediol Production by Acetogenic Bacteria, an Alternative Route to Chemical Synthesis, Using Industrial Waste Gas. Applied and environmental microbiology, 77(15), 5467-75(2011).

Leang, C., Ueki, T., Nevin, K. P., & Lovley, D. R. A Genetic System for Clostridium ljungdahlii: A Chassis for Autotrophic Production of Biocommodities and a Model Homoacetogen. Applied and environmental microbiology, (Nov. 2012).

Mermelstein, L. D., Welker, N. E., Bennett, G. N., & Papoutsakis, E. T. Expression of cloned homologous fermentative genes in Clostridium acetobutylicum ATCC 824. Bio/technology (Nature Publishing Company), 10(2), 190-195(1992).

Perez, J. M., Richter, H., Loftus, S. E., & Angenent, L. T. Biocatalytic reduction of short-chain carboxylic acids into their corresponding alcohols with syngas fermentation. Biotechnology and bioengineering, 1-30(2012).

Strätz, M., Sauer, U., Kuhn, a, & Dürre, P. Plasmid Transfer into the Homoacetogen Acetobacterium woodii by Electroporation and Conjugation. Applied and environmental microbiology, 60(3), 1033-7(1994).

Tanner, R. S., Miller, L. M., & Yang, D. *Clostridium ljungdahlii* sp. nov., an acetogenic species in clostridial rRNA homology group I. International journal of systematic bacteriology, 43(2), 232(1993).

Tyurin, Michael, & Kiriukhin, M. Electrofusion of cells of Acetogen *Clostridium* sp. MT 351 with erm (B) or cat in the chromosome. Journal of Biotech, 1-12(2012).

Tyurin, MV, Desai, S., & Lynd, L. Electrotransformation of Clostridium thermocellum. Applied and environmental mictrobiology 70(2), 883-890(2004).

Williams, D. R., Young, D. I., & Young, M. Conjugative plasmid transfer from *Escherichia coli* to Clostridium acetobutylicum. Journal of general microbiology, 136(5), 819-26(1990).

Tirado-Acevedo O. Production of Bioethanol from Synthesis Gas Using Clostridium ljungdahlii. PhD thesis, North Carolina State University, 2010.

Murray, N.E. et al. (2000) Microbial. Molec. Biol. Rev. 64, 412.

Köpke & Dürre, Biochemical production of biobutanol, In: Handbook of biofuels production: processes and technologies (Eds.: Luque, Campelo & Clark), Woodhead Publishing Ltd, Camebridge, UK: 221-257 (2011).

Ismail et al., J. Bacteriol, 1993, 175: 5079-5105.

Office Action, Japanese Patent Application 2015-516270, Japanese Patent Office, dated Mar. 21, 2017.

Kopke, Fermentative production of ethanol from carbon monoxide, Curr Opin Biotechnol, 22: 320-325, 2011.

Li, Microbial production of meso-2,3-butanediol by metabolically engineered *Escherichia coli* under low oxygen condition, Appl Microbiol Biotechnol, 87: 2001-2009, 2010.

Lee, Synthsis of pure-2,3-butanediol from crude glycerol using an engineered metabolic pathway in *Escherichia coli*, Appl Biochem Biotechnol, 166: 1801-1813, 2012.

Multer, Production of methyl ethyl ketone from biomass using a hybrid biochemical/catalytic approach, Ind Eng Chem Res, 52: 56-60, 2012.

Search Report for European Patent Application No. 13800454.4, European Patent Office, dated Nov. 27, 2015.

* cited by examiner

SEQUENCE LISTING

```
<160> NUMBER OF SEQ ID NOS: 40

<210> SEQ ID NO 1
<211> LENGTH: 479
<212> TYPE: DNA
<213> ORGANISM: Clostridium autoethanogenum

<400> SEQUENCE: 1

aatatgatat ttatgtccat tgtgaaaggg attatattca actattattc cagttacgtt      60

catagaaatt ttcctttcta aaatatttta ttccatgtca agaactctgt ttatttcatt     120

aaagaactat aagtacaaag tataaggcat ttgaaaaaat aggctagtat attgattgat     180

tatttatttt aaaatgccta agtgaaatat atacatatta taacaataaa ataagtatta     240

gtgtaggatt tttaaataga gtatctattt tcagattaaa tttttgatta tttgatttac     300

attatataat attgagtaaa gtattgacta gcaaaatttt ttgatacttt aatttgtgaa     360

atttcttatc aaaagttata tttttgaata atttttattg aaaaatacaa ctaaaaagga     420

ttatagtata agtgtgtgta attttgtgtt aaatttaaag ggaggaaatg aacatgaaa      479


<210> SEQ ID NO 2
<211> LENGTH: 28
<212> TYPE: DNA
<213> ORGANISM: Artificial Sequence
<220> FEATURE:
<223> OTHER INFORMATION: Oligonucleotide Ppta-ack-NotI-F

<400> SEQUENCE: 2

gagcggccgc aatatgatat ttatgtcc                                         28


<210> SEQ ID NO 3
<211> LENGTH: 28
<212> TYPE: DNA
<213> ORGANISM: Artificial Sequence
<220> FEATURE:
<223> OTHER INFORMATION: Oligonucleotide Ppta-ack-NdeI-R

<400> SEQUENCE: 3

ttccatatgt ttcatgttca tttcctcc                                         28


<210> SEQ ID NO 4
```

<211> LENGTH: 2951
<212> TYPE: DNA
<213> ORGANISM: Artificial Sequence
<220> FEATURE:
<223> OTHER INFORMATION: codon optimised pddABC operon

<400> SEQUENCE: 4

```
catatgagaa gtaaaagatt tgaggcatta gcaaaaagac cagttaatca agatggattt     60
gtaaaagaat ggattgaaga aggtttcata gcaatggaat ctccaaatga tccaaaacca    120
agtattaaaa ttgtaaatgg tgctgtaaca gaacttgatg gaaaacctgt atctgatttt    180
gacttaatag atcattttat agcaagatat ggaataaact taaatagagc tgaagaagtt    240
atggctatgg atagtgttaa acttgctaat atgctttgtg atcctaatgt aaaaagatct    300
gagattgtac ctttaactac agcaatgact cctgctaaga tagtagaagt tgtatcacac    360
atgaatgtag tagagatgat gatggcaatg cagaaaatga gagctagaag aactccatca    420
caacaagcac atgtaactaa cgttaaagat aacccagtac aaatagcagc agatgctgca    480
gaaggtgctt ggagaggttt tgacgaacaa gaaactacag ttgcagttgc aagatatgct    540
ccttttaatg ctattgctct tttagttgga tcacaggttg gtagaccagg tgtacttaca    600
caatgtagtt tagaagaagc tactgagctt aaattaggaa tgcttggaca tacatgttat    660
gcagaaacta taagtgttta cggaacagaa cctgttttta cagatggtga tgatactcca    720
tggtctaagg gatttcttgc atcatcatac gcatcaagag gtttaaagat gagatttact    780
tctggatctg gatctgaagt tcagatggga tatgctgaag gtaagagtat gttatatctt    840
gaagctagat gtatatatat aacaaaagct gcaggtgttc aaggattaca aaacggatca    900
gtatcatgca taggtgtacc aagtgcagtt ccatcaggaa ttagagctgt tcttgctgaa    960
aacttaatat gtagttcatt agatttagag tgcgcaagtt ctaatgatca gacatttact   1020
cattcagata tgagaagaac agctagatta cttatgcagt ttcttcctgg aactgatttc   1080
ataagttctg gatattcagc tgtacctaat tacgataata tgtttgctgg aagtaatgaa   1140
gatgctgaag actttgatga ttataatgta atacaaagag acttaaaggt agacggtggt   1200
ttaagaccag taagagaaga agatgtaata gcaataagaa ataaggctgc tagagcactt   1260
caggcagtat tcgcaggtat gggtttacct cctataacag atgaagaagt tgaagcagct   1320
acttatgctc atggttctaa ggatatgcct gaaagaaata ttgttgaaga tataaagttc   1380
gctcaggaaa ttataaataa gaatagaaat ggacttgaag tagttaaagc attagcacag   1440
ggtggtttta ctgatgttgc acaagatatg cttaatattc agaaagctaa attaactggt   1500
gattatttac acacatcagc aataattgtt ggtgacggac aagtattatc agcagtaaac   1560
gatgtaaatg actatgctgg accagctaca ggatatagac ttcaaggtga aagatgggaa   1620
gagataaaga atataccagg tgcacttgat ccaaatgaaa tagattaatt gaacacacaa   1680
aaaaaataat taataaggag gcaaacaaat ggaaataaat gaaaaacttt taagacagat   1740
aattgaagat gtactttcag aaatgaaagg aagtgataaa cctgtatcat ttaatgcacc   1800
tgctgctagt gcagctcctc aagcaactcc tcctgctggt gacggattct taactgaagt   1860
tggtgaagct agacaaggaa cacaacaaga tgaagtaata atagctgttg gaccagcatt   1920
tggattagct cagactgtaa atatagtagg tattccacac aaatcaatac ttagagaagt   1980
tatagctgga atagaagaag aaggtataaa ggcaagagtt attagatgtt ttaagtcttc   2040
tgatgtagca tttgttgctg ttgaaggtaa tagactttct ggatcaggaa taagtattgg   2100
aatacaatca aaaggaacaa cagttattca tcagcaagga ttaccaccac ttagtaacct   2160
```

```
tgaacttttt cctcaagcac cattattaac attagagact tatagacaaa taggtaagaa   2220

tgctgctaga tacgcaaaaa gagagtcacc acagccagta ccaactttaa acgatcaaat   2280

ggcaagacct aaatatcagg caaaatctgc aattttacat ataaaagaga ctaaatatgt   2340

agtaacagga aagaatccac aggaacttag agtagcatta taaaaataaa tagtagatat   2400

ataaagtaaa aggaggtaag ataatgaata cagacgcaat agaatcaatg gtaagagatg   2460

tactttcaag aatgaactct ttacaaggag aagctccagc agcagctcca gcagcaggtg   2520

gtgcaagtag aagtgctaga gtttcagatt atccattagc taataagcat cctgaatggg   2580

ttaaaactgc aacaaacaaa actttagatg attttactct tgaaaatgtt ctttcaaata   2640

aagtaactgc tcaggatatg agaattactc cagaaacact tagattacag gctagtatag   2700

ctaaggatgc tggaagagac agattagcta tgaattttga aagagcagct gagttaactg   2760

ctgttcctga tgatagaata ttagaaatat acaatgctct tagaccttat agatctacaa   2820

aagaagaact tttagcaata gcagatgatc ttgagtctag atatcaagca aaaatttgtg   2880

cagcattcgt aagagaagca gctacacttt atgtagagag aaagaaatta aaaggagatg   2940

attaagaatt c                                                        2951
```

```
<210> SEQ ID NO 5
<211> LENGTH: 780
<212> TYPE: DNA
<213> ORGANISM: Artificial Sequence
<220> FEATURE:
<223> OTHER INFORMATION: codon optimised budC gene

<400> SEQUENCE: 5

catatgaaaa aggttgcatt agttacagga gcaggacaag gtataggaaa ggctatagca     60

cttagacttg taaaagatgg atttgcagtt gctattgcag attataacga tactacagct    120

aaagcagttg cttcagaaat taatcaagca ggtggtagag caatggctgt aaaagttgat    180

gttagtgata gagaccaggt tttgctgct gttgaacaag ctagaaagac attaggtggt    240

tttgatgtaa tagttaataa tgctggtgta gctccatcaa ctccaattga atctataact    300

ccagaaatag tagacaaagt atataatata aacgtaaaag gtgtaatatg gggtatacaa    360

gcagcagtag aagcattcaa gaaagaagga cacggtggta aaataataaa tgcttgttct    420

caggctggtc atgtaggtaa tccagaatta gcagtatact catcatcaaa gtttgcagta    480

agaggtctta cacaaacagc agctagagat cttgctccat taggaattac agtaaatgga    540

tattgccctg gaattgttaa gactcctatg tgggcagaga ttgatagaca agtttctgag    600

gctgcaggta aacctttagg atatggaact gcagagtttg caaagagaat tactcttggt    660

agacttagtg aacctgaaga tgttgcagct tgtgtaagtt atttagcttc acctgatagt    720

gattatatga caggacagtc tcttttaatt gacggtggta tggtatttaa ttaagaattc    780
```

```
<210> SEQ ID NO 6
<211> LENGTH: 2254
<212> TYPE: DNA
<213> ORGANISM: Artificial Sequence
<220> FEATURE:
<223> OTHER INFORMATION: codon optimised ddrAB operon

<400> SEQUENCE: 6

gagctcagga ggtttactca tgagatatat agctggaata gatataggaa atagtagtac     60

tgaagtagca ttagcaactt tagatgaagc tggagcatta actataactc atagtgcatt    120
```

-continued

```
agcagaaact actggaataa aaggaacttt aagaaatgta tttggaatac aagaagcatt    180
agcattagta gcaagaggag ctggaatagc agtaagtgat ataagtttaa taagaataaa    240
tgaagcaact cctgtaatag gagatgtagc aatggaaact ataactgaaa ctataataac    300
tgaaagtact atgataggac ataatcctaa aacacctgga ggagcaggat taggaactgg    360
aataactata acacctcaag aattattaac tagacctgca gatgcacctt atatattagt    420
agtaagtagt gcatttgatt ttgcagatat agcaagtgta ataaatgcaa gtttaagagc    480
aggatatcaa ataactggag taatattaca aagagatgat ggagtattag taagtaatag    540
attagaaaaa cctttaccta tagtagatga agttttatat atagatagaa tacctttagg    600
aatgttagca gcaatagaag tagcagtacc tggaaaagta atagaaactt taagtaatcc    660
ttatggaata gcaactgtat ttaatttaag tcctgaagaa actaaaaata tagtacctat    720
ggcaagagca ttaataggaa atagatctgc agtagtagta aaaactccta gtggagatgt    780
aaaagcaaga gcaatacctg ctggaaattt agaattatta gcacaaggaa gatctgtaag    840
agtagatgta gctgctggag ctgaagcaat aatgaaagca gtagatggat gtggaagatt    900
agataatgta actggagaaa gtggaacaaa tataggagga atgttagaac atgtaagaca    960
aactatggca gaattaacta ataaacctag tagtgaaata tttatacaag atttattagc   1020
agtagatact agtgtacctg taagtgtaac tggaggatta gctggagaat ttagtttaga   1080
acaagcagta ggaatagcaa gtatggtaaa aagtgataga ttacaaatgg caatgatagc   1140
aagagaaata gaacaaaaat taaatataga tgtacaaata ggaggagcag aagcagaagc   1200
agcaatatta ggagcattaa caacacctgg aactactaga cctttagcaa tattagattt   1260
aggagcagga tctactgatg caagtataat aaatcctaaa ggagatataa tagcaactca   1320
tttagctgga gctggagata tggtaactat gataatagct agagaattag gattagaaga   1380
tagatattta gcagaagaaa taaaaaaata tcctttagca aaagtagaaa gtttatttca   1440
tttaagacat gaagatggaa gtgtacaatt ttttagtact cctttacctc ctgcagtatt   1500
tgcaagagta tgtgtagtaa aagcagatga attagtacct ttacctggag atttagcatt   1560
agaaaaagta agagctataa gaagatctgc aaaagaaaga gtatttgtaa ctaatgcatt   1620
aagagcttta agacaagtaa gtcctactgg aaatataaga gatataccttttgtagtatt   1680
agttggagga agtagtttag attttgaagt acctcaatta gtaactgatg cattagcaca   1740
ttatagatta gtagctggaa gaggaaatat aagaggatct gaaggaccta gaaatgcagt   1800
agcaacagga ttaatattaa gttggcataa agaatttgca catgaaagat aacaatgtag   1860
gaggttaact atgaatggaa atcatagtgc accagcaata gcaatagcag taatagatgg   1920
atgtgatgga ttatggagag aagtattatt aggaatagaa gaagaaggaa taccttttag   1980
attacaacat catcctgctg gagaagtagt agatagtgca tggcaagcag caagaagtag   2040
tcctttatta gtaggaatag catgtgatag acatatgtta gtagtacatt ataaaaattt   2100
acctgcaagt gcacctttat ttactttaat gcatcatcaa gatagtcaag cacatagaaa   2160
tactggaaat aatgcagcaa gattagtaaa aggaatacca tttagagatt taaatagtga   2220
agcaactgga gaacaacaag atgaataagg tacc                                2254
```

<210> SEQ ID NO 7
<211> LENGTH: 25
<212> TYPE: DNA
<213> ORGANISM: Artificial Sequence
<220> FEATURE:
<223> OTHER INFORMATION: Oligonucleotide als-NdeI-F

<400> SEQUENCE: 7
ggaagtttca tatgaataga gatat 25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide als-EcoR1-R

<400> SEQUENCE: 8
ggaagtttca tatgaataga gatat 25

<210> SEQ ID NO 9
<211> LENGTH: 32
<212> TYPE: DNA
<213> ORGANISM: Artificial Sequence
<220> FEATURE:
<223> OTHER INFORMATION: Oligonucleotide als-NdeI-F

<400> SEQUENCE: 9
gcgaattcga catagaggtg aatgtaatat gg 32

<210> SEQ ID NO 10
<211> LENGTH: 33
<212> TYPE: DNA
<213> ORGANISM: Artificial Sequence
<220> FEATURE:
<223> OTHER INFORMATION: Oligonucleotide als-EcoR1-R

<400> SEQUENCE: 10
gcgagctctt atttttcaac acttgttatc tca 33

<210> SEQ ID NO 11
<211> LENGTH: 9052
<212> TYPE: DNA
<213> ORGANISM: Artificial Sequence
<220> FEATURE:
<223> OTHER INFORMATION: plasmid pMTL007C-E5-2,3bdh-468469s

<400> SEQUENCE: 11
cctgcagggt gtagtagcct gtgaaataag taaggaaaaa aaagaagtaa gtgttatata 60
tgatgattat tttgtagatg tagataggat aatagaatcc atagaaaata taggttatac 120
agttatataa aaattacttt aaaaattaat aaaaacatgg taaaatataa atcgtataaa 180
gttgtgtaat ttttaagcta aaaaagctta taattatcct tagcactcgt tgaggtgcgc 240
ccagataggg tgttaagtca agtagtttaa ggtactactc tgtaagataa cacagaaaac 300
agccaaccta accgaaaagc gaaagctgat acgggaacag agcacggttg gaaagcgatg 360
agttacctaa agacaatcgg gtacgactga gtcgcaatgt taatcagata taaggtataa 420
gttgtgttta ctgaacgcaa gtttctaatt tcgattagtg ctcgatagag gaaagtgtct 480
gaaacctcta gtacaaagaa aggtaagtta ggctcaacga cttatctgtt atcaccacat 540
ttgtacaatc tggtacaatc tgtaggagaa cctatgggaa cgaaacgaaa gcgatgccga 600
gaatctgaat ttaccaagac ttaacactaa ctggggatac cctaaacaag aatgcctaat 660
agaaaggagg aaaaaggcta tagcactaga gcttgaaaat cttgcaaggg tacggagtac 720
tcgtagtagt ctgagaaggg taacgccctt tacatggcaa aggggtacag ttattgtgta 780
ctaaaattaa aaattgatta gggaggaaaa cctcaaaatg aaaccaacaa tggcaatttt 840

```
agaaagaatc agtaaaaatt cacaagaaaa tatagacgaa gtttttacaa gactttatcg    900
ttatctttta cgtccagata tttattacgt ggcgacgcgt gaagttccta tactttctag    960
agaataggaa cttcgcgact catagaatta tttcctcccg ttaaataata gataactatt   1020
aaaaatagac aatacttgct cataagtaac ggtacttaaa ttgtttactt tggcgtgttt   1080
cattgcttga tgaaactgat ttttagtaaa cagttgacga tattctcgat tgacccattt   1140
tgaaacaaag tacgtatata gcttccaata tttatctgga acatctgtgg tatggcgggt   1200
aagttttatt aagacactgt ttacttttgg tttaggatga aagcattccg ctggcagctt   1260
aagcaattgc tgaatcgaga cttgagtgtg caagagcaac cctagtgttc ggtgaatatc   1320
caaggtacgc ttgtagaatc cttcttcaac aatcagatag atgtcagacg catggctttc   1380
aaaaaccact tttttaataa tttgtgtgct taaatggtaa ggaatactcc caacaatttt   1440
atacctctgt ttgttaggga attgaaactg tagaatatct tggtgaatta aagtgacacg   1500
agtattcagt tttaattttt ctgacgataa gttgaataga tgactgtcta attcaataga   1560
cgttacctgt ttacttattt tagccagttt cgtcgttaaa tgccctttac ctgttccaat   1620
ttcgtaaacg gtatcggttt cttttaaatt caattgtttt attatttggt tgagtacttt   1680
ttcactcgtt aaaaagtttt gagaatattt tatatttttg ttcataccag caccagaagc   1740
accagcatct cttgggttaa ttgaggcctg agtataaggt gacttatact tgtaatctat   1800
ctaaacgggg aacctctcta gtagacaatc ccgtgctaaa ttgtaggact gccctttaat   1860
aaatacttct atatttaaag aggtatttat gaaaagcgga atttatcaga ttaaaaatac   1920
tttctctaga gaaaatttcg tctggattag ttacttatcg tgtaaaatct gataaatgga   1980
attggttcta cataaatgcc taacgactat ccctttgggg agtagggtca agtgactcga   2040
aacgatagac aacttgcttt aacaagttgg agatatagtc tgctctgcat ggtgacatgc   2100
agctggatat aattccgggg taagattaac gaccttatct gaacataatg ccatatgaat   2160
ccctcctaat ttatacgttt tctctaacaa cttaattata cccactatta ttatttttat   2220
caatatagaa gttcctatac tttctagaga ataggaactt cacgcgttgg gaaatggcaa   2280
tgatagcgaa acaacgtaaa actcttgttg tatgctttca ttgtcatcgt cacgtgattc   2340
ataaacacaa gtgaatgtcg acagtgaatt tttacgaacg aacaataaca gagccgtata   2400
ctccgagagg ggtacgtacg gttcccgaag agggtggtgc aaaccagtca cagtaatgtg   2460
aacaaggcgg tacctcccta cttcaccata tcattttctg cagcccccta gaaataattt   2520
tgtttaactt taagaaggag atatacatat atggctagat cgtccattcc gacagcatcg   2580
ccagtcacta tggcgtgctg ctagcgctat atgcgttgat gcaatttcta tgcactcgta   2640
gtagtctgag aagggtaacg ccctttacat ggcaaagggg tacagttatt gtgtactaaa   2700
attaaaaatt gattagggag gaaaacctca aaatgaaacc aacaatggca attttagaaa   2760
gaatcagtaa aaattcacaa gaaaatatag acgaagtttt tacaagactt tatcgttatc   2820
ttttacgtcc agatatttat tacgtggcgt atcaaaattt atattccaat aaaggagctt   2880
ccacaaaagg aatattagat gatacagcgg atggctttag tgaagaaaaa ataaaaaaga   2940
ttattcaatc tttaaaagac ggaacttact atcctcaacc tgtacgaaga atgtatattg   3000
caaaaaagaa ttctaaaaag atgagacctt taggaattcc aactttcaca gataaattga   3060
tccaagaagc tgtgagaata attcttgaat ctatctatga accggtattc gaagatgtgt   3120
ctcacggttt tagacctcaa cgaagctgtc acacagcttt gaaaacaatc aaaagagagt   3180
ttggcggcgc aagatggttt gtggagggag atataaaagg ctgcttcgat aatatagacc   3240
```

```
acgttacact cattggactc atcaatctta aaatcaaaga tatgaaaatg agccaattga   3300
tttataaatt tctaaaagca ggttatctgg aaaactggca gtatcacaaa acttacagcg   3360
gaacacctca aggtggaatt ctatctcctc ttttggccaa catctatctt catgaattgg   3420
ataagtttgt tttacaactc aaaatgaagt ttgaccgaga aagtccagaa agaataacac   3480
ctgaatatcg ggagctccac aatgagataa aaagaatttc tcaccgtctc aagaagttgg   3540
agggtgaaga aaaagctaaa gttcttttag aatatcaaga aaaacgtaaa agattaccca   3600
cactccccctg tacctcacag acaaataaag tattgaaata cgtccggtat gcggacgact   3660
tcattatctc tgttaaagga agcaaagagg actgtcaatg gataaaagaa caattaaaac   3720
tttttattca taacaagcta aaaatggaat tgagtgaaga aaaaacactc atcacacata   3780
gcagtcaacc cgctcgtttt ctgggatatg atatacgagt aaggagatct ggaacgataa   3840
aacgatctgg taaagtcaaa aagagaacac tcaatgggag tgtagaactc cttattcctc   3900
ttcaagacaa aattcgtcaa tttatttttg acaagaaaat agctatccaa aagaaagata   3960
gctcatggtt tccagttcac aggaaatatc ttattcgttc aacagactta gaaatcatca   4020
caatttataa ttctgaactc cgcgggattt gtaattacta cggtctagca agtaatttta   4080
accagctcaa ttattttgct tatcttatgg aatacagctg tctaaaaacg atagcctcca   4140
aacataaggg aacactttca aaaaccattt ccatgtttaa agatggaagt ggttcgtggg   4200
ggatcccgta tgagataaag caaggtaagc agcgccgtta ttttgcaaat tttagtgaat   4260
gtaaatcccc ttatcaattt acggatgaga taagtcaagc tcctgtattg tatggctatg   4320
cccggaatac tcttgaaaac aggttaaaag ctaaatgttg tgaattatgt gggacgtctg   4380
atgaaaatac ttcctatgaa attcaccatg tcaataaggt caaaaatctt aaaggcaaag   4440
aaaaatggga aatggcaatg atagcgaaac aacgtaaaac tcttgttgta tgctttcatt   4500
gtcatcgtca cgtgattcat aaacacaagt gaatgtcgag cacccgttct cggagcactg   4560
tccgaccgct ttggccgccg cccagtcctg ctcgcttcgc tacttggagc cactatcgac   4620
tacgcgatca tggcgaccac acccgtcctg tggatcgcca agccgccgat ggtagtgtgg   4680
ggtctcccca tgcgagagta gggaactgcc aggcatcaaa taaaacgaaa ggctcagtcg   4740
aaagactggg cctttcgttt tatctgttgt ttgtcggtga acgctctcct gagtaggaca   4800
aatccgccgg gagcggattt gaacgttgcg aagcaacggc ccggagggtg gcgggcagga   4860
cgcccgccat aaactgccag gcatcaaatt aagcagaagg ccatcctgac ggatggcctt   4920
tttgcgtttc tacaaactct tcctgtcgtc atatctacaa gccatccccc cacagatacg   4980
ggcgcgccgc cattattttt ttgaacaatt gacaattcat ttcttatttt ttattaagtg   5040
atagtcaaaa ggcataacag tgctgaatag aaagaaattt acagaaaaga aaattataga   5100
atttagtatg attaattata ctcatttatg aatgtttaat tgaatacaaa aaaaaatact   5160
tgttatgtat tcaattacgg gttaaaatat agacaagttg aaaaatttaa taaaaaaata   5220
agtcctcagc tcttatatat taagctacca acttagtata taagccaaaa cttaaatgtg   5280
ctaccaacac atcaagccgt tagagaactc tatctatagc aatatttcaa atgtaccgac   5340
atacaagaga aacattaact atatatattc aatttatgag attatcttaa cagatataaa   5400
tgtaaattgc aataagtaag atttagaagt ttatagcctt tgtgtattgg aagcagtacg   5460
caaaggcttt tttatttgat aaaaattaga agtatattta ttttttcata attaatttat   5520
gaaaatgaaa gggggtgagc aaagtgacag aggaaagcag tatcttatca aataacaagg   5580
```

-continued

```
tattagcaat atcattattg actttagcag taaacattat gacttttata gtgcttgtag   5640

ctaagtagta cgaaaggggg agctttaaaa agctccttgg aatacataga attcataaat   5700

taatttatga aaagaagggc gtatatgaaa acttgtaaaa attgcaaaga gtttattaaa   5760

gatactgaaa tatgcaaaat acattcgttg atgattcatg ataaaacagt agcaacctat   5820

tgcagtaaat acaatgagtc aagatgttta cataaaggga aagtccaatg tattaattgt   5880

tcaaagatga accgatatgg atggtgtgcc ataaaaatga gatgttttac agaggaagaa   5940

cagaaaaaag aacgtacatg cattaaatat tatgcaagga gctttaaaaa agctcatgta   6000

aagaagagta aaaagaaaaa ataatttatt tattaattta atattgagag tgccgacaca   6060

gtatgcacta aaaaatatat ctgtggtgta gtgagccgat acaaaaggat agtcactcgc   6120

attttcataa tacatcttat gttatgatta tgtgtcggtg ggacttcacg acgaaaaccc   6180

acaataaaaa aagagttcgg ggtagggtta agcatagttg aggcaactaa acaatcaagc   6240

taggatatgc agtagcagac cgtaaggtcg ttgtttaggt gtgttgtaat acatacgcta   6300

ttaagatgta aaaatacgga taccaatgaa gggaaaagta taatttttgg atgtagtttg   6360

tttgttcatc tatgggcaaa ctacgtccaa agccgtttcc aaatctgcta aaaagtatat   6420

cctttctaaa atcaaagtca agtatgaaat cataaataaa gtttaatttt gaagttatta   6480

tgatattatg tttttctatt aaaataaatt aagtatatag aatagtttaa taatagtata   6540

tacttaatgt gataagtgtc tgacagtgtc acagaaagga tgattgttat ggattataag   6600

cggccggcca gtgggcaagt tgaaaaattc acaaaaatgt ggtataatat ctttgttcat   6660

tagagcgata aacttgaatt tgagagggaa cttagatggt atttgaaaaa attgataaaa   6720

atagttggaa cagaaaagag tattttgacc actactttgc aagtgtacct tgtacctaca   6780

gcatgaccgt taaagtggat atcacacaaa taaaggaaaa gggaatgaaa ctatatcctg   6840

caatgcttta ttatattgca atgattgtaa accgccattc agagtttagg acggcaatca   6900

atcaagatgg tgaattgggg atatatgatg agatgatacc aagctataca atatttcaca   6960

atgatactga aacattttcc agcctttgga ctgagtgtaa gtctgacttt aaatcatttt   7020

tagcagatta tgaaagtgat acgcaacggt atggaaacaa tcatagaatg gaaggaaagc   7080

caaatgctcc ggaaaacatt tttaatgtat ctatgatacc gtggtcaacc ttcgatggct   7140

ttaatctgaa tttgcagaaa ggatatgatt atttgattcc tatttttact atggggaaat   7200

attataaaga agataacaaa attatacttc ctttggcaat tcaagttcat cacgcagtat   7260

gtgacggatt tcacatttgc cgttttgtaa acgaattgca ggaattgata aatagttaac   7320

ttcaggtttg tctgtaacta aaaacaagta tttaagcaaa aacatcgtag aaatacggtg   7380

tttttgtta ccctaagttt aaactccttt ttgataatct catgaccaaa atcccttaac   7440

gtgagttttc gttccactga gcgtcagacc ccgtagaaaa gatcaaagga tcttcttgag   7500

atcctttttt tctgcgcgta atctgctgct tgcaaacaaa aaaaccaccg ctaccagcgg   7560

tggtttgttt gccggatcaa gagctaccaa ctctttttcc gaaggtaact ggcttcagca   7620

gagcgcagat accaaatact gttcttctag tgtagccgta gttaggccac cacttcaaga   7680

actctgtagc accgcctaca tacctcgctc tgctaatcct gttaccagtg gctgctgcca   7740

gtggcgataa gtcgtgtctt accgggttgg actcaagacg atagttaccg gataaggcgc   7800

agcggtcggg ctgaacgggg ggttcgtgca cacagcccag cttggagcga acgacctaca   7860

ccgaactgag atacctacag cgtgagctat gagaaagcgc cacgcttccc gaagggagaa   7920

aggcggacag gtatccggta agcggcaggg tcggaacagg agagcgcacg agggagcttc   7980
```

```
caggggaaa cgcctggtat ctttatagtc ctgtcgggtt tcgccacctc tgacttgagc   8040

gtcgattttt gtgatgctcg tcaggggggc ggagcctatg gaaaaacgcc agcaacgcgg   8100

cctttttacg gttcctggcc ttttgctggc cttttgctca catgttcttt cctgcgttat   8160

cccctgattc tgtggataac cgtattaccg cctttgagtg agctgatacc gctcgccgca   8220

gccgaacgac cgagcgcagc gagtcagtga gcgaggaagc ggaagagcgc ccaatacgca   8280

gggcccccctg cttcggggtc attatagcga ttttttcggt atatccatcc tttttcgcac   8340

gatatacagg attttgccaa agggttcgtg tagactttcc ttggtgtatc caacggcgtc   8400

agccgggcag gataggtgaa gtaggcccac ccgcgagcgg gtgttccttc ttcactgtcc   8460

cttattcgca cctggcggtg ctcaacggga atcctgctct gcgaggctgg ccggctaccg   8520

ccggcgtaac agatgagggc aagcggatgg ctgatgaaac caagccaacc aggaagggca   8580

gcccacctat caaggtgtac tgccttccag acgaacgaag agcgattgag gaaaaggcgg   8640

cggcggccgg catgagcctg tcggcctacc tgctggccgt cggccagggc tacaaaatca   8700

cgggcgtcgt ggactatgag cacgtccgcg agctggcccg catcaatggc gacctgggcc   8760

gcctgggcgg cctgctgaaa ctctggctca ccgacgaccc gcgcacggcg cggttcggtg   8820

atgccacgat cctcgccctg ctggcgaaga tcgaagagaa gcaggacgag cttggcaagg   8880

tcatgatggg cgtggtccgc ccgagggcag agccatgact tttttagccg ctaaaacggc   8940

cggggggtgc gcgtgattgc caagcacgtc cccatgcgct ccatcaagaa gagcgacttc   9000

gcggagctgg tgaagtacat caccgacgag caaggcaaga ccgatcgggc cc           9052
```

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide Og42f

<400> SEQUENCE: 12

```
ctgcacctaa aaccaaagca gtatt                                          25
```

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide Og43r

<400> SEQUENCE: 13

```
atcctttaag caagagtact gcacc                                          25
```

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide fD1

<400> SEQUENCE: 14

```
ctgcacctaa aaccaaagca gtatt                                          25
```

<210> SEQ ID NO 15
<211> LENGTH: 25
<212> TYPE: DNA
<213> ORGANISM: Artificial Sequence
<220> FEATURE:

<223> OTHER INFORMATION: Oligonucleotide rP2

<400> SEQUENCE: 15
atcctttaag caagagtact gcacc 25

<210> SEQ ID NO 16
<211> LENGTH: 1160
<212> TYPE: DNA
<213> ORGANISM: Clostridium autoethanogenum

<400> SEQUENCE: 16

```
agtggcactg gaaaagaact cttagctcaa tctattcaca attatagtga aagatgtgaa      60
ggccctttg tagctataaa ttgtagttct atacctagag aacttgtaga aagtgagctt     120
tttggttatg aaaaaggagc ttttacggga gctttaaagc aaggaaagcc tggaaagttt    180
gaattagcag atggaggaac tatttttttg gatgaagtag gagagcttcc tcttgatata    240
cagtcaaagc ttttaagggt tcttgataat aataaaatta caagagttgg aggaacttat    300
gaaaaacagc taaatgtaag gataatagga gctacaaaca gggtgctcaa ggatgaaatt    360
aaaaagaaaa atttcagaag tgacctttat tatagattga gtgtgatgaa tataaaaact    420
gtcccactta gggaaagaaa agaagatata gagcttttaa ttaaatattt tatggaagaa    480
ttgaattcta aaagtttgtg taagaagaaa gtagtggaaa aagcatacat agaaaagatt    540
aaagcttatg attggcctgg aaatgttaga gaacttagaa atgtaataga gagggattac    600
tatttaagtg aggataagat ggcccctttg gattatttag aaaaagaagt ttatgaaaaa    660
aatgtctcct ctgatccagt aaatattagt gtgcttccaa tggatgtttt agaaaaagaa    720
aacattgaaa atgcacttaa aaagtgtaag ggaaatatat taaaagctgc aaaatcttta    780
aatatcagta gatctaccat gtatagaaaa atgaaaaagt atggaataaa aagtgtgtca    840
aaatgaccag aaaagagtaa gattctcaaa ataggacact aagtatgtgt cataatggca    900
catagtgatt ttaaatgtct ttttaacagg tttcttgttt ttggtatggc ttttgcttat    960
aaaatatagt gaatatatta acaggtatat gtaaatttta atattgccat actattataa   1020
aaaaggagag ataattatga aagctgtatt gtggtatgat aaaaaagatg taagagtaga   1080
ggaaattgag gaacctaagg taaaagaaaa tgctgtaaaa attaaagtga aatggtgtgg   1140
tatatgtggt tctgacttgc                                               1160
```

<210> SEQ ID NO 17
<211> LENGTH: 834
<212> TYPE: DNA
<213> ORGANISM: Clostridium autoethanogenum

<400> SEQUENCE: 17

```
tattgaggag gccaaaaatg agctttaaga aaaatgtata cgatacaatg agggaactaa     60
tatctgtgcc aagcatatct ggtacaaaag aagagtgtgc ggcagcagaa aaaatatatg    120
aaaaaatttt ggaaatacct tattttaagg acaatcctga aaatctagga atagagcaaa    180
ttgaagatga tcctttagga agaagctttg tatgggcagt agtaaatgga aatgaaaatt    240
caccaaattc gtttatactt tcaggtcatt tggatgtagt tggagtagaa gaatttggac    300
atttaaaatc tatggctttt gatgtagatg aatgtactaa aagaatctca gaattgaatt    360
tagatgaaga tgctatggag gattttaaat caggagattg gatatttgga aggggaactg    420
cagacatgaa gtttggagtg gccctcaata tggaactttt aagagaattc agtaaagaga    480
gaaactttaa gggaaactta ttacttttag tagttcctgg tgaagagagt aattccgaag    540
```

```
gaatgattgc tgcagctcca tttcttctta aattaaagga agagaggaag tacaattact    600

gtggtatgat aatatcagag ccaagtatac ctgaaagagg agaaaaagaa ggcaagagat    660

tatatatagg tagtgtaggt aaaattatgc ctttattttt ttgtgtggga aaagaaactc    720

atgtagggga atctttaaga ggattgaatc caaatttgct agtttcagag ataaacaaat    780

taatggaatg taatccagat ctctcagata gcgtttatga tactgtgact ccac          834


<210> SEQ ID NO 18
<211> LENGTH: 39
<212> TYPE: DNA
<213> ORGANISM: Artificial Sequence
<220> FEATURE:
<223> OTHER INFORMATION: Oligonucleotide Og13f

<400> SEQUENCE: 18

attcatcctg caggagtggc actggaaaag aactcttag                            39


<210> SEQ ID NO 19
<211> LENGTH: 37
<212> TYPE: DNA
<213> ORGANISM: Artificial Sequence
<220> FEATURE:
<223> OTHER INFORMATION: Oligonucleotide Og14r

<400> SEQUENCE: 19

gactgcggcc gcgcaagtca gaaccacata taccaca                              37


<210> SEQ ID NO 20
<211> LENGTH: 35
<212> TYPE: DNA
<213> ORGANISM: Artificial Sequence
<220> FEATURE:
<223> OTHER INFORMATION: Oligonucleotide Og15f

<400> SEQUENCE: 20

atatgctagc tattgaggag gccaaaaatg agctt                                35


<210> SEQ ID NO 21
<211> LENGTH: 37
<212> TYPE: DNA
<213> ORGANISM: Artificial Sequence
<220> FEATURE:
<223> OTHER INFORMATION: Oligonucleotide Og16r

<400> SEQUENCE: 21

gactggcgcg ccgtggagtc acagtatcat aaacgct                              37


<210> SEQ ID NO 22
<211> LENGTH: 25
<212> TYPE: DNA
<213> ORGANISM: Artificial Sequence
<220> FEATURE:
<223> OTHER INFORMATION: Oligonucleotide Og33f

<400> SEQUENCE: 22

aatggcaggg cagataattg taatg                                           25


<210> SEQ ID NO 23
<211> LENGTH: 25
<212> TYPE: DNA
<213> ORGANISM: Artificial Sequence
<220> FEATURE:
<223> OTHER INFORMATION: Oligonucleotide Og34r
```

<400> SEQUENCE: 23
aaggcattct gagccagttc tttta 25

<210> SEQ ID NO 24
<211> LENGTH: 1062
<212> TYPE: DNA
<213> ORGANISM: Clostridium autoethanogenum

<400> SEQUENCE: 24
acagttaaaa agcatatcta acagtccttc cactgtacta attcaaggcg aaagcggtac 60
aggtaaagaa cttattgcgc agtccatcca caatgacagc agcagaaaaa ataacagctt 120
tatagcaata aattgcggtg ccatacccaa aaatttaata gaaagtgaat tattcggata 180
tgaagatgga tcattcacag gtgcaaaaca tggagggcgt gcaggaaaat ttgaacttgc 240
aaatggtggt actttatttt tagatgaaat tggggaaatg cctttagata tgcaagtaaa 300
tcttttaaga gttctccaag aaaactgtat tacaagaata ggcgggaaca gatgtgtaaa 360
aatagatata agaatcattg cagctactaa taaaaattg agggaagaaa tacataaagg 420
aacttttcgc gaagatttat actatagact aaatgtaata cctatatatg taccaccact 480
gcgggaaaga gatatggata ttaaaatact gataaactat tttttaaaga taaaagcttt 540
taaacttaaa aaacctattc caatagtaag acctgatata tatcaaaagc tcttaaatta 600
taattggccc ggaaatgtaa gagaattgga aaattgtatt gaaaatatcg taaatatgaa 660
tggaaataca tctttcaact tcgaaaatag tatttcagta aatacgcaaa ctagtccttg 720
tactacaaaa tttaaatatg atatgtattc attaaaagag ttggaaaaag aagcaataac 780
aaattgtatg agtaattgca atggtaacat tgcaaaagct tctaaaattc tgggaataaa 840
tagaagtact ttgtatacaa aaataaaaaa atatcaaatt aatttttctt aaagtgtatg 900
taaacacaac tttgttgtaa aaagcaacat tattttctta aaaaatgttg ctttttacag 960
catttttcaa ttatatatat taaccttata aagtcctacc cccctaaatt caaccttttc 1020
atgataaaaa acatactggc acaacatttg cttatatatt ta 1062

<210> SEQ ID NO 25
<211> LENGTH: 823
<212> TYPE: DNA
<213> ORGANISM: Clostridium autoethanogenum

<400> SEQUENCE: 25
cgtattttta attgcgaact taagatttaa ttaatatcta ctatgagtaa gtcaacatat 60
atacctaaat tatgataaaa ttatatatta taatttcaaa ataaacataa ctataataat 120
acactaagat aaagctattt atctgatggc tacctactgt aacactccct cttctatcaa 180
agtgagagat aacagtagct acgcccctag ataattcatc taaacttagt gggagaaaca 240
aaactctaaa gagaaagcga ttcactttaa atcaaagatt tgagatatct gcttctccca 300
ctaagtaaga ttcattgata taaaaaggaa ggtaatctaa taatgtttaa accatttact 360
catagtgaaa tagtcagtag gtctcttaat agatgcatta aataccatat agaaaaaggt 420
ataccaaaac ctaaacgaac acttagtcgc aaagaattgg acaacttaat aaaagaaaac 480
aacgatatta taaaaatagc aaaaccattt atggaaatac tttatgattt tttaagtgga 540
tcaggtttct cattatatct cacagacaaa aatggaattg tattaactat cataggtgac 600
aaagatattg taatggagca ggcaaaggct ggaatagcag aaggtattga tctgagtgaa 660
caaagtgcag gtacaaatgc agcaggaact gctattttttg aaaatttgtc agttcaactt 720

```
tcaggcaaag aacattttat aaatactttt cagatttata cctgctctgc atctgtcata    780

cataacgaac aaggaaatat aatcggatgt ctaactttaa ctg                      823


<210> SEQ ID NO 26
<211> LENGTH: 39
<212> TYPE: DNA
<213> ORGANISM: Artificial Sequence
<220> FEATURE:
<223> OTHER INFORMATION: Oligonucleotide Sec5f

<400> SEQUENCE: 26

attcatcctg caggacagtt aaaaagcata tctaacagt                            39


<210> SEQ ID NO 27
<211> LENGTH: 37
<212> TYPE: DNA
<213> ORGANISM: Artificial Sequence
<220> FEATURE:
<223> OTHER INFORMATION: Oligonucleotide Sec5r

<400> SEQUENCE: 27

gactgcggcc gctaaatata taagcaaatg ttgtgcc                              37


<210> SEQ ID NO 28
<211> LENGTH: 34
<212> TYPE: DNA
<213> ORGANISM: Artificial Sequence
<220> FEATURE:
<223> OTHER INFORMATION: Oligonucleotide Sec3f

<400> SEQUENCE: 28

atatgctagc gtatttttaa ttgcgaactt aaga                                 34


<210> SEQ ID NO 29
<211> LENGTH: 36
<212> TYPE: DNA
<213> ORGANISM: Artificial Sequence
<220> FEATURE:
<223> OTHER INFORMATION: Oligonucleotide Sec3r

<400> SEQUENCE: 29

gactggcgcg ccagttaaag ttagacatcc gattat                               36


<210> SEQ ID NO 30
<211> LENGTH: 25
<212> TYPE: DNA
<213> ORGANISM: Artificial Sequence
<220> FEATURE:
<223> OTHER INFORMATION: Oligonucleotide Sec0f

<400> SEQUENCE: 30

ttggaatttt agctgtagat aacaa                                           25


<210> SEQ ID NO 31
<211> LENGTH: 25
<212> TYPE: DNA
<213> ORGANISM: Artificial Sequence
<220> FEATURE:
<223> OTHER INFORMATION: Oligonucleotide Sec0r

<400> SEQUENCE: 31

taagtgattt tcaatggact ttact                                           25


<210> SEQ ID NO 32
```

```
<211> LENGTH: 344
<212> TYPE: DNA
<213> ORGANISM: Artificial Sequence
<220> FEATURE:
<223> OTHER INFORMATION: intron target region against alcohol
      dehydrogenase

<400> SEQUENCE: 32

aagcttataa ttatccttag atatcaatct tgtgcgccca gatagggtgt taagtcaagt     60

agtttaaggt actactctgt aagataacac agaaaacagc caacctaacc gaaaagcgaa    120

agctgatacg ggaacagagc acggttggaa agcgatgagt tacctaaaga caatcgggta    180

cgactgagtc gcaatgttaa tcagatataa ggtataagtt gtgtttactg aacgcaagtt    240

tctaatttcg attatatctc gatagaggaa agtgtctgaa acctctagta caaagaaagg    300

taagttagca agattgactt atctgttatc accacatttg taca                     344


<210> SEQ ID NO 33
<211> LENGTH: 25
<212> TYPE: DNA
<213> ORGANISM: Artificial Sequence
<220> FEATURE:
<223> OTHER INFORMATION: Oligonucleotide of SecCTf

<400> SEQUENCE: 33

tgattttagg ccatgaagct gtagg                                           25


<210> SEQ ID NO 34
<211> LENGTH: 24
<212> TYPE: DNA
<213> ORGANISM: Artificial Sequence
<220> FEATURE:
<223> OTHER INFORMATION: Oligonucleotide of SecCTr

<400> SEQUENCE: 34

catgatttgt tcaactatat cacc                                            24


<210> SEQ ID NO 35
<211> LENGTH: 20
<212> TYPE: DNA
<213> ORGANISM: Artificial Sequence
<220> FEATURE:
<223> OTHER INFORMATION: Oligonucleotide GnK-F

<400> SEQUENCE: 35

tcaggacctt ctggaactgg                                                 20


<210> SEQ ID NO 36
<211> LENGTH: 20
<212> TYPE: DNA
<213> ORGANISM: Artificial Sequence
<220> FEATURE:
<223> OTHER INFORMATION: Oligonucleotide GnK-R

<400> SEQUENCE: 36

acctcccctt ttcttggaga                                                 20


<210> SEQ ID NO 37
<211> LENGTH: 20
<212> TYPE: DNA
<213> ORGANISM: Artificial Sequence
<220> FEATURE:
<223> OTHER INFORMATION: Oligonucleotide FoT4L-F

<400> SEQUENCE: 37
```

-continued

```
caggtttcgg tgctgaccta                                             20


<210> SEQ ID NO 38
<211> LENGTH: 20
<212> TYPE: DNA
<213> ORGANISM: Artificial Sequence
<220> FEATURE:
<223> OTHER INFORMATION: Oligonucleotide FoT4L-F

<400> SEQUENCE: 38

aactccgccg ttgtatttca                                             20


<210> SEQ ID NO 39
<211> LENGTH: 20
<212> TYPE: DNA
<213> ORGANISM: Artificial Sequence
<220> FEATURE:
<223> OTHER INFORMATION: Oligonucleotide KpBDH -F

<400> SEQUENCE: 39

aagtttctga ggctgcaggt                                             20


<210> SEQ ID NO 40
<211> LENGTH: 20
<212> TYPE: DNA
<213> ORGANISM: Artificial Sequence
<220> FEATURE:
<223> OTHER INFORMATION: Oligonucleotide KpBDH -R

<400> SEQUENCE: 40

aagtttctga ggctgcaggt                                             20
```

RECOMBINANT MICROORGANISMS AND USES THEREFOR

CROSS REFERENCE TO RELATED APPLICATION

This application claims the benefit of U.S. provisional application No. 61/657,292 filed on Jun. 8, 2012 which is incorporated by reference in its entirety.

FIELD OF THE INVENTION

The present invention relates to recombinant microorganisms and methods for the production of MEK and/or 2-butanol by microbial fermentation of a substrate comprising CO.

BACKGROUND OF THE INVENTION 2-butanol is an organic compound that is produced on a large scale, primarily as a precursor to the industrial solvent methyl ethyl ketone (MEK or butanone). It is typically produced from a petrochemical (butene), by hydration using a sulfuric acid catalyst.

MEK is an important ingredient in paints and inks, with a global market of US$2 billion that is growing at 1.9% per annum. As an intermediate in its synthesis, demand for 2-butanol is closely linked to demand for butanone. Importantly, 2-butanol can also be converted to 1,3-butadiene, which is used in synthetic rubbers, resins and adhesives. The global market for 1,3-butadiene exceeds US$19 billion, and it is growing at 2.7% per annum. 2-butanol, which is more energy dense than ethanol also has potential use as a fuel as well as a precursor for butadiene production.

It is an object of the invention to provide recombinant microorganisms and a method for the production of MEK and/or 2-butanol by microbial fermentation which may provide one or more advantages over known methods, or to at least to provide the public with a useful choice.

SUMMARY OF INVENTION

The invention generally provides, inter alia, methods for the production of MEK and/or 2-butanol by microbial fermentation of a substrate comprising CO and/or $CO_2$, and recombinant microorganisms of use in such methods.

In a first aspect, the invention provides a carboxydotrophic acetogenic recombinant microorganism capable of producing MEK and/or 2-butanol and optionally one or more other products by fermentation of a substrate comprising CO.

In one particular embodiment, the microorganism is adapted to express one or more enzymes (or one or more subunits thereof) in the MEK and/or 2-butanol biosynthesis pathways which are not present in a parental microorganism from which the recombinant microorganism is derived.

In another embodiment, the microorganism is adapted to over-express one or more enzymes (or one or more subunits thereof) in the MEK and/or 2-butanol biosynthesis pathways which are present in a parental microorganism from which the recombinant microorganism is derived.

In one embodiment, the microorganism is adapted to express one or more enzymes (or one or more subunits thereof) in the MEK and/or 2-butanol biosynthesis pathways which are not present in a parental microorganism and over-express one or more enzymes (or one or more subunits thereof) in the MEK and/or 2-butanol biosynthesis pathways which are present in a parental microorganism.

In one embodiment, the microorganism is adapted to express one or more of the following:

An enzyme which catalyses the conversion of (R)-Acetoin to (R,S)-2,3-butanediol;

An enzyme which catalyses the conversion of (R,S)-2,3-butanediol to MEK; and,

An enzyme which catalyses the conversion of MEK to 2-butanol.

In one embodiment, the microorganism is adapted to reduce or substantially eliminate the activity of one or more enzymes which are present in a parental microorganism. In one embodiment, the one or more enzymes are a part of the MEK and/or 2-butanol biosynthesis pathways.

In one embodiment, the microorganism is capable of producing 2-butanol by fermentation of a substrate comprising CO and is adapted to express or overexpress one or more enzymes in the 2-butanol biosynthesis pathway chosen from:

(S)-2,3-butanediol dehydrogenase;

diol/glycerol dehydratase;

Alcohol dehydrogenase; and, a functionally equivalent variant of any one or more thereof.

In one embodiment, the parental microorganism lacks (S)-2,3-butanediol dehydrogenase and diol/glycerol dehydratase or a functionally equivalent variant of any one or more thereof and the recombinant microorganism is adapted to express both these enzymes.

In one embodiment, the parental microorganism comprises (R)-2,3-butanediol dehydrogenase or a functionally equivalent variant thereof and the recombinant microorganism is adapted to reduce or substantially eliminate the activity of this enzyme.

In one embodiment, the microorganism is capable of producing MEK by fermentation of a substrate comprising CO and is adapted to express or overexpress one or more enzymes in the MEK biosynthesis pathway chosen from:

(S)-2,3-butanediol dehydrogenase;

Diol/glycerol dehydratase; and, a functionally equivalent variant of any one or more thereof.

In one embodiment, the parental microorganism lacks (S)-2,3-butanediol dehydrogenase and diol/glycerol dehydratase or a functionally equivalent variant of any one or more thereof and the recombinant microorganism is adapted to express both these enzymes.

In one embodiment, the parental microorganism comprises alcohol dehydrogenase or a functionally equivalent variant thereof and the recombinant microorganism is adapted to reduce or substantially eliminate the activity of this enzyme.

In one embodiment, the parental microorganism comprises (R)-2,3-butanediol dehydrogenase or a functionally equivalent variant thereof and the recombinant microorganism is adapted to reduce or substantially eliminate the activity of this enzyme.

In one embodiment, the microorganism comprises one or more exogenous nucleic acids adapted to increase expression of one or more nucleic acids present in the parental microorganism and which one or more nucleic acids encode one or more of the enzymes (or one or more subunits thereof) referred to herein before. In one embodiment, the one or more exogenous nucleic acid adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster or Phosphotransacetylase/Acetate kinase operon promoters.

In one embodiment, the microorganism comprises one or more exogenous nucleic acids adapted to express one or more of the enzymes (or one or more subunits thereof) referred to herein before which are not present in the parental microorganism. In one embodiment, the microorganisms comprise one or more exogenous nucleic acid encoding and adapted to express at least two or three of the enzymes (or one or more subunits thereof).

In one embodiment, the one or more exogenous nucleic acid is a nucleic acid construct or vector, in one particular embodiment a plasmid, encoding one or more of the enzymes referred to hereinbefore in any combination. In one embodiment, the exogenous nucleic acid is an expression plasmid.

In one embodiment, the microorganism comprises one or more exogenous nucleic acids adapted to increase expression of one or more nucleic acids present in the parental microorganism and one or more exogenous nucleic acids adapted to express one or more enzymes not present in the parental microorganism. In another embodiment, the microorganism comprises one or more nucleic acids adapted to reduce or substantially eliminate the activity of an enzyme present in the parental microorganism.

In one particular embodiment, the parental microorganism is selected from the group of carboxydotrophic acetogenic bacteria comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii*, and *Thermoanaerobacter kiuvi*.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks the activity of one or more of the following:

an enzyme which catalyses the conversion of (R)-Acetoin to (R,S)-2,3-butanediol;

an enzyme which catalyses the conversion of (R,S)-2,3-butanediol to MEK; and, an enzyme which catalyses the conversion of MEK to 2-butanol.

In one embodiment, the parental microorganism lacks one or more genes encoding one or more of the following:

an enzyme which catalyses the conversion of (R)-Acetoin to (R,S)-2,3-butanediol;

an enzyme which catalyses the conversion of (R,S)-2,3-butanediol to MEK; and, an enzyme which catalyses the conversion of MEK to 2-butanol.

In one embodiment, the parental microorganism lacks one or more genes encoding (S)-2,3-butanediol dehydrogenase, Diol/glycerol dehydratase, and alcohol dehydrogenase, and/or a functionally equivalent variant of any one or more thereof.

In one embodiment, the parental microorganism comprises one or more genes encoding (R)-2,3-butanediol dehydrogenase, alcohol dehydrogenase, and/or a functionally equivalent variant of any one or more thereof.

In one embodiment, the parental microorganism comprises one or more genes encoding encoding (R)-2,3-butanediol dehydrogenase, alcohol dehydrogenase, or a functionally equivalent variant of any one or more thereof and lacks one or more genes encoding (S)-2,3-butanediol dehydrogenase, Diol/glycerol dehydratase, and/or a functionally equivalent variant of any one or more thereof.

In a second aspect, the invention provides a nucleic acid encoding one or more enzymes (or one or more subunits thereof) which when expressed in a microorganism allows the microorganism to produce MEK and/or 2-butanol by fermentation of substrate comprising CO.

In one embodiment, the nucleic acid encodes two or more enzymes (or one or more subunits thereof) which when expressed in a microorganism allows the microorganism to produce MEK and/or 2-butanol by fermentation of substrate comprising CO.

In one embodiment, the nucleic acid encodes one or more enzyme chosen from the group consisting of:

an enzyme which catalyses the conversion of (R)-Acetoin to (R,S)-2,3-butanediol;

an enzyme which catalyses the conversion of (R,S)-2,3-butanediol to MEK; and, an enzyme which catalyses the conversion of MEK to 2-butanol.

In one embodiment, the enzymes are chosen from (S)-2,3-butanediol dehydrogenase, Diol/glycerol dehydratase, alcohol dehydrogenase, and/or a functionally equivalent variant of any one or more thereof.

In one embodiment, the nucleic acid comprises nucleic acid sequences encoding (S)-2,3-butanediol dehydrogenase, Diol/glycerol dehydratase, and/or a functionally equivalent variant of any one or more thereof, in any order.

In one embodiment, the nucleic acids of the invention further comprise a promoter. In one embodiment, the promoter allows for constitutive expression of the genes under its control. In a particular embodiment a Wood-Ljungdahl cluster promoter is used. In another particular embodiment, a Phosphotransacetylase/Acetate kinase operon promoter is used. In one particular embodiment, the promoter is from *C. autoethanogenum*.

In another aspect, the invention provides a nucleic acid adapted to reduce or eliminate the expression of (R)-2,3-butanediol dehydrogenase, alcohol dehydrogenase and/or a functionally equivalent variant of any one or more thereof in a parental microorganism.

In another aspect, the invention provides a nucleic acid adapted to increase the expression of one or more of (S)-2,3-butanediol dehydrogenase, Diol/glycerol dehydratase, alcohol dehydrogenase and/or a functionally equivalent variant of any one or more thereof, when present in a parental microorganism.

In a third aspect, the invention provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the invention provides host organisms comprising any one or more of the nucleic acids of the second aspect or vectors or constructs of the third aspect.

In a fifth aspect, the invention provides a composition comprising an expression construct or vector as referred to in the third aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In a sixth aspect, the invention provides a method for the production of MEK and/or 2-butanol, and optionally one or more other products, by microbial fermentation comprising fermenting a substrate comprising CO using a recombinant microorganism of the first aspect of the invention.

In one embodiment the method comprises the steps of:

(a) providing a substrate comprising CO to a bioreactor containing a culture of one or more microorganism of the first aspect of the invention; and
(b) anaerobically fermenting the culture in the bioreactor to produce at least MEK and/or 2-butanol.

In one embodiment the method comprises the steps of:

a. capturing CO-containing gas produced as a result of the industrial process, before the gas is released into the atmosphere;
b. anaerobically fermenting the CO-containing gas to produce at least MEK and/or 2-butanol by a culture containing one or more microorganism of the first aspect of the invention.

In particular embodiments of the method aspects, the microorganism is maintained in an aqueous culture medium.

In particular embodiments of the method aspects, the fermentation of the substrate takes place in a bioreactor.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering MEK and/or 2-butanol and optionally one or more other products from the fermentation broth.

In a seventh aspect, the invention provides MEK and/or 2-butanol when produced by the method of the sixth aspect.

In another aspect, the invention provides a method for the production of a microorganism of the first aspect of the invention comprising transforming a parental microorganism with one or more exogenous nucleic acid such that the microorganism is capable of producing MEK and/or 2-butanol, and optionally one or more other products, by fermentation of a substrate comprising CO, wherein the parental microorganism is not capable of producing MEK and/or 2-butanol by fermentation of a substrate comprising CO.

In one particular embodiment, a parental microorganism is transformed with one or more exogenous nucleic acid adapted to express one or more enzymes in the MEK and/or 2-butanol biosynthesis pathway which are not present in the parental microorganism. In another embodiment, a parental microorganism is transformed with one or more nucleic acid adapted to over-express one or more enzymes in the MEK and/or 2-butanol biosynthesis pathway which are present in the parental microorganism. In another embodiment, a parental microorganism is transformed with one or more exogenous nucleic acid adapted to express one or more enzymes in the MEK and/or 2-butanol biosynthesis pathway which are not present in the parental microorganism and over-express one or more enzymes in the MEK and/or 2-butanol biosynthesis pathway which are naturally present in the parental microorganism. In another embodiment, a parental microorganism is transformed to reduce or substantially eliminate the activity of one or more enzyme which can convert 2-butanone to 2-butanol and/or one or more enzyme which can convert (R)-acetoin to (R,R)-2,3-butanediol. In one embodiment, a parental microorganism is transformed to express or overexpress one or more enzymes and reduce or substantially eliminate the activity of one or more other enzymes.

In certain embodiments, the one or more enzymes are as herein before described.

In certain embodiment, the parental microorganism is as herein before described.

Isolated, genetically engineered, carboxydotrophic, acetogenic bacteria are provided which comprise an exogenous nucleic acid encoding a meso-2,3-butanediol dehydrogenase enzyme and an exogenous nucleic acid encoding a diol/glycerol dehydratase enzyme. The bacteria express the enzymes from these nucleic acids. The two enzymes may be expressed in the same bacteria or they may be present separately in different bacteria. In general the bacteria the bacteria do not express the enzymes in nature. In some cases, the bacteria have a knock-out mutation in a D-(−)2,3-butanediol dehydrogenase gene. In other cases, the bacteria may further comprise an exogenous nucleic acid encoding a reactivation protein of the diol/glycerol dehydratase. These extend the active life of the dehydratase which can lose activity after prolonged contact with its substrate and/or product. Typically the bacteria can express the enzymes under anaerobic conditions.

The bacteria may, in some embodiments further comprise a knock-out mutation in its alcohol dehydrogenase gene. This can diminish or prevent expression of the encoded alcohol dehydrogenase enzyme. Such a mutation will reduce or prevent the formation of 2-butanol, causing a build up of MEK. MEK may be the desired product of the fermentation, so this mutation may be highly desirable. The bacteria may in some embodiments further comprise a knock-out mutation in its D-(−)2,3-butanediol dehydrogenase. This will reduce or prevent the formation of an isomer of butanediol that is not desirable for production of MEK or 2-butanol. Optionally, the bacteria may further comprise an exogenous nucleic acid encoding a reactivation protein of diol/glycerol dehydratase. This will help keep the production of MEK from meso-2,3-butanediol at desirable levels.

A plasmid is also provided which can be used to transform the carboxydotrophic, acetogenic bacteria useful in the fermentations and conversions described here. The plasmid can replicate in carboxydotrophic, acetogenic bacteria, i.e., it has a suitable origin of replication. In some cases, the plasmid will comprise a nucleic acid encoding a meso-2,3-butanediol dehydrogenase enzyme and a nucleic acid encoding a diol/glycerol dehydratase enzyme, although either may be present separately in a plasmid. When the plasmid is transformed into the bacteria, desirably the bacteria express the enzymes. Alternatively they can be expressed only when induced, if an inducible promoter is used for expression.

Such bacteria and plasmids are useful in practicing a process for converting CO and/or CO2 into 2-butanol. A gaseous CO-containing and/or CO2-containing substrate is passed to a bioreactor containing a culture of the carboxydotrophic, acetogenic bacteria described above. The bacteria are grown in a culture medium under conditions such that the bacteria convert the CO and/or CO2 to 2-butanol. Butanol may be recovered from the bioreactor either in a continuous or in an episodic fashion.

Some of the bacteria discussed above are well adapted for use in a process for converting CO and/or CO2 into methyl ethyl ketone (MEK). As discussed above, the bacteria will desirably have a mutation decreasing or diminishing the activity or production of alcohol dehydrogenase. In the process, a gaseous CO-containing and/or CO2-containing substrate is passed to a bioreactor containing a culture of the appropriate carboxydotrophic, acetogenic bacteria. The bacteria are grown in a culture medium under conditions such that the bacteria convert the CO and/or CO2 to MEK. The MEK can be recovered from the bioreactor using any known process, whether continuously or saltitorily. In some cases the bacteria used will have a knock-out mutation in a D-(−)-2,3-butanediol dehydrogenase gene, to diminish production of side products. In other cases the bacteria may further comprise an exogenous nucleic acid encoding a reactivation protein of the diol/glycerol dehydratase. This will keep the step of conversion of meso-2,3-butanediol to MEK robust. In some cases the bacteria will have both a knock-out mutation in a D-(−)-2,3-butanediol dehydrogenase gene and an exogenous nucleic acid encoding a reactivation protein of the diol/glycerol dehydratase.

Nucleic acids are also provided which can be used for transformation and expression in bacteria of choice. One useful nucleic acid encodes a meso-2,3-butanediol dehydrogenase codon-optimized for *Clostridium autoethanogenum*. Another useful nucleic acid encodes a diol/glycerol dehydratase codon-optimized for *Clostridium autoethanogenum*. In one particular example, the meso-2,3-butanediol dehydrogenase is *Klebsiella pneumoniae* meso-2,3-butanediol dehydrogenase. In another particular example the nucleic acid encodes a *Klebsiella oxytoca* diol/glycerol dehydratase. In another particular example the nucleic acid encodes a *Klebsiella oxytoca* diol/glycerol dehydratase. These various encoding sequences may be on a single or multiple molecules, such as one or more plasmids. If multiple plasmids are to be used, their origins of replication will desirably by compatible. The nucleic acids may also be carried on appropriate bacteriophage.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which.

DETAILED DESCRIPTION OF THE INVENTION

Figure 1:
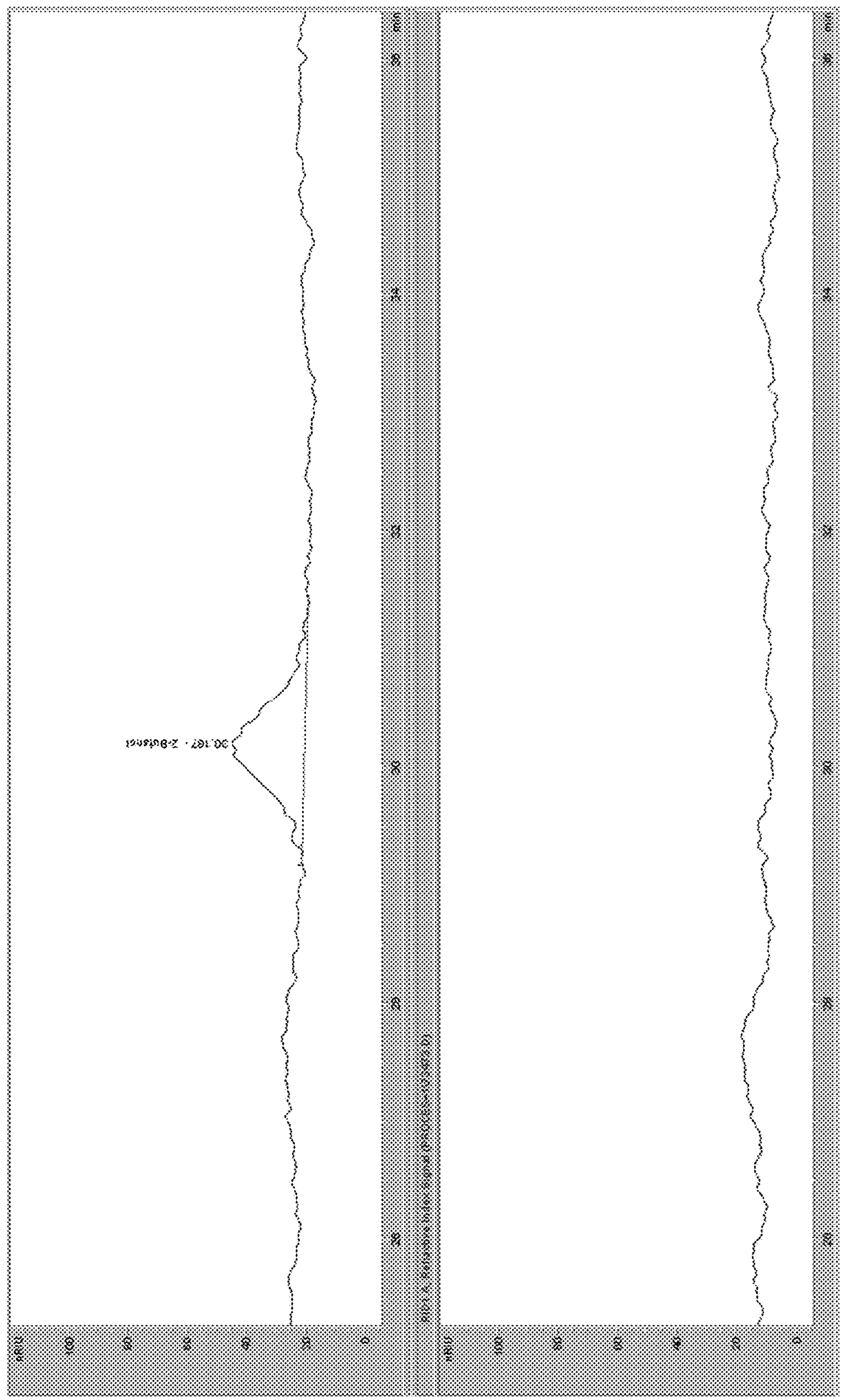
FIG. 1: Sample chromatograms showing 2-butanol peak. Top chromatogram is of sample from *C. autoethanogenum* harbouring the plasmid containing pddABC with meso-2,3-butanediol added to the medium. Bottom chromatogram is of sample from wild-type *C. autoethanogenum* with meso-2,3-butanediol added to the medium.

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventors contemplate the production of MEK and/or 2-butanol using recombinant microorganisms adapted to express or overexpress key enzymes in the MEK and/or 2-butanol biosynthesis pathways from (R)-acetoin by fermentation on substrates comprising CO. They have demonstrated the production of 2-butanol from (R,S)-2,3-butanediol in the carboxydotrophic acetogen *Clostridium autoethanogenum*, and the conversion of (R)-acetoin to (S)-2,3-butanediol, which is an intermediate step in the production of both MEK and 2-butanol. This offers an alternative means for the production of MEK and/or 2-butanol which may have benefits over the current methods for the production of MEK and/or 2-butanol. In addition, it offers a means of using carbon monoxide from industrial processes which would otherwise be released into the atmosphere and pollute the environment.

Carboxydotrophic acetogenic microorganisms are not known to produce MEK and/or 2-butanol. They lack the biosynthesis pathways to make these products. In addition, they produce the intermediate (R,R)-2,3-butanediol whereas the production of MEK and 2-butanol requires production of the intermediate (R,S)-2,3-butanediol.

While the inventors have demonstrated the efficacy of the invention in *Clostridium autoethanogenum*, they contemplate that the invention is applicable to the wider group of carboxydotrophic acteogenic microorganisms and fermentation on substrates comprising CO, as discussed above and further herein.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency," "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for a substrate comprising CO to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO." However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting," "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of microorganisms which differ from the organism to which they are to be introduced, or they may be artificially or recombinantly created. In one embodiment, the exogenous nucleic acids represent nucleic acid sequences already (by way of example only, naturally) present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not normally (by way of example only, naturally) present within the microorganism to which they are to be introduced and allow for the expression of a product not present within the microorganism or increased expression of a gene already present (by way of example only, a native gene) in the microorganism (for example in the case of introduction of a regulatory element such as a promoter). The exogenous nucleic acid may be adapted to integrate into the genome of the microorganism to which it is to be introduced or to remain in an extra-chromosomal state.

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants". By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium* sp., *Clostridium ljungdahlii, Clostridium butyricum, Clostridium diolis, Roseburia inulinivorans, Klebsiella oxytoca, Salmonella enterica, Citobacter koseri, Klebsiella pneumoniae* and *Escherichia coli*, details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants". A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using any number of known methods. However, by way of example, the methods outlined in *Biochem. Biophys. Res. Commun.,* 1976, 69: 475-80, in *Arch. Biochem. Biophys.* 1986:245:144-52, or in *J. Bacteriol,* 1993, 175: 5079-5105 may be used to measure the activity of Alcohol dehydrogenase, diol/glycerol dehydratase, (S)-2,3-butanediol dehydrogenase, and (R)-2,3-butanediol dehydrogenase, respectively.

"Over-express," "over expression," and like terms and phrases when used in relation to the invention should be taken broadly to include any increase in expression of one or more protein (including one or more nucleic acid encoding one or more protein) as compared to the expression level of the protein (including one or more nucleic acid) of a parental microorganism under the same conditions. It should not be taken to mean that the protein (including one or more nucleic acid) is expressed at any particular level.

A "parental microorganism" is a microorganism used to generate a recombinant microorganism of the invention. The parental microorganism may be one that occurs in nature (ie a wild type microorganism) or one that has been previously modified but which does not express or over-express one or more of the enzymes the subject of the present invention. Accordingly, the recombinant microorganisms of the invention have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

Figure 8:
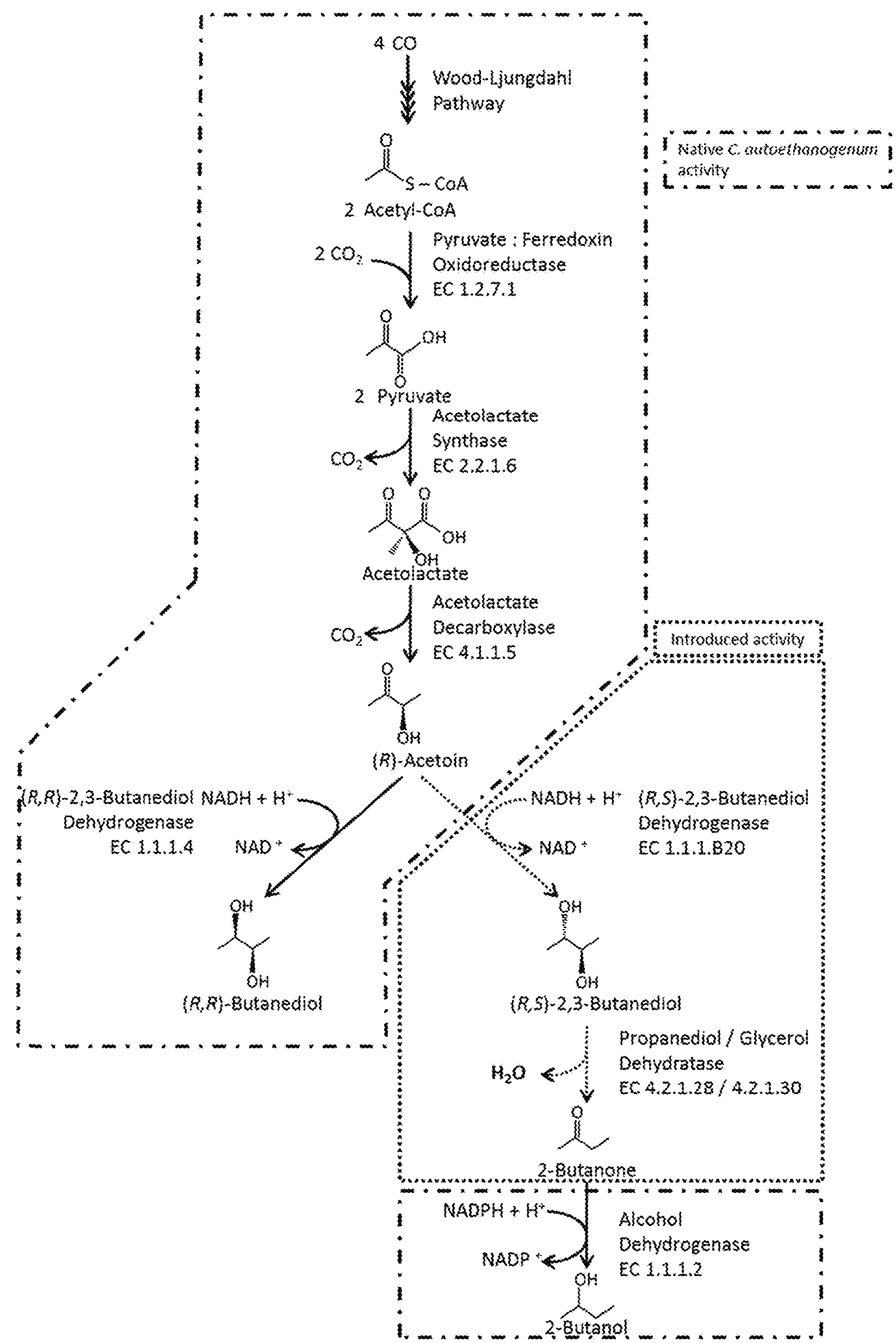
FIG. 8: Pathway for production of meso-2,3-BDO, MEK and 2-butanol from CO.
Figure 9:
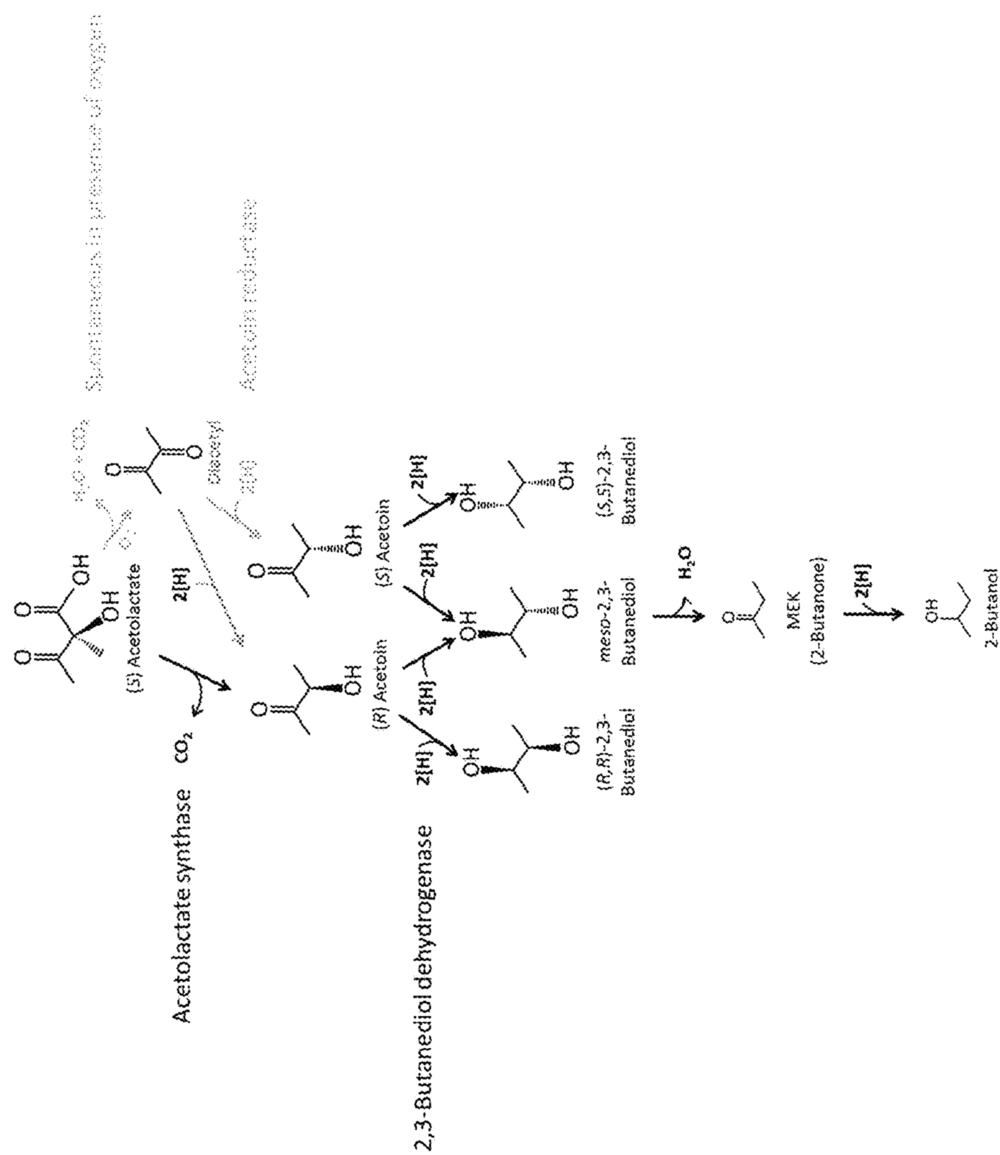
FIG. 9: Pathway for production of meso-2,3-BDO, MEK and 2-butanol.

The "meso-2,3-butanediol biosynthesis pathway" is the enzymatic pathway allowing for the conversion of (R)-Acetoin to meso-2,3-butanediol. By way of example, the pathway may include the steps of conversion of (R)-Acetoin to (R,S)-2,3-butanediol. By way of example, a (S)-2,3-butanediol dehydrogenase may catalyse the conversion of (R)-Acetoin to (R,S)-2,3-butanediol and a diol/glycerol dehydratase may catalyse the conversion of (R,S)-2,3-butanediol to MEK (FIGS. 8 and 9).

The "MEK biosynthesis pathway" is the enzymatic pathway allowing for the conversion of (R)-Acetoin to MEK. By way of example, the pathway may include the steps of conversion of (R)-Acetoin to (R,S)-2,3-butanediol, and (R,S)-2,3-butanediol to MEK. By way of example, a (S)-2,3-butanediol dehydrogenase may catalyse the conversion of (R)-Acetoin to (R,S)-2,3-butanediol and a diol/glycerol dehydratase may catalyse the conversion of (R,S)-2,3-butanediol to MEK. (FIGS. 8 and 9).

The "2-butanol biosynthesis pathway" is the enzymatic pathway allowing for the conversion of (R)-Acetoin to 2-butanol. By way of example, the pathway may include the steps of conversion of (R)-Acetoin to (R,S)-2,3-butanediol, (R,S)-2,3-butanediol to MEK, and MEK to 2-butanol. By way of example, a (S)-2,3-butanediol dehydrogenase may catalyse the conversion of Acetoin to (R,S)-2,3-butanediol, a diol/glycerol dehydratase may catalyse the conversion of (R,S)-2,3-butanediol to MEK and an alcohol dehydrogenase may catalyse MEK to 2-butanol. (FIGS. 8 and 9).

Unless the context clearly requires otherwise, reference to an enzyme in the MEK and/or 2-butanol biosynthesis pathway should be taken to include reference to any one or more subunit of the enzyme. By way of example only, propanediol/glycerol dehydratase may comprise three subunits.

Reference to a "diol/glycerol dehydratase" should be taken to include reference to a diol dehydratase and separately a glycerol dehydratase. It should not be taken to imply that a single enzyme has both activities. In one particular embodiment the diol/glycerol dehydratase is a propanediol/glycerol dehydratase.

In certain embodiments, the invention involves reducing or substantially eliminating the activity of certain enzymes. For example, carboxydotrophic acetogens may naturally convert (R)-acetoin to (R,R)-2,3-butanediol (using the enzyme (R)-2,3-butanediol dehydrogenase), whereas for the production of MEK and 2-butanol, the production of (R,S)-2,3-butanediol is required. Reducing the production of (R,R)-2,3-butanediol may help increase the efficiency of the fermentation to produce MEK and/or 2-butanol. Similarly, carboxydotrophic acetogens may naturally convert MEK to 2-butanol (using an alcohol dehydrogenase, for example). This may assist in the production of 2-butanol but may reduce the amount of MEK that can be recovered. Reducing the activity of the alcohol dehydrogenase may assist in increasing the amount of MEK that can be recovered from a fermentation.

"Reduce or substantially eliminate" the activity of an enzyme should be taken broadly to include any reduction in the level of activity of the enzyme. It may include genetic modification to disrupt the expression and/or activity of the enzyme. In one embodiment, the one or more genetic modification disrupts or knocks out one or more of the genes encoding the enzyme. In one embodiment, the one or more genetic modification disrupts the activity of a compound required for the expression or activity of the enzyme. In one embodiment, the one or more genetic modification increases the expression or activity of one or more compounds which inhibit the expression or activity of the enzyme.

A "genetic modification which disrupts" a gene, expression or activity of an enzyme (and like terms) in accordance with the invention should be taken broadly to include any genetic modification which at least reduces the biosynthesis of a product which the enzyme catalyses. The phrase should be taken to include, for example: modification to a gene encoding the enzyme, including a modification to a genetic regulatory element involved in the expression of a gene; introduction of a nucleic acid which produces a protein which reduces or inhibits the activity of the enzyme, or which reduces or prevents expression of the enzyme; introduction of a nucleic acid which expresses a nucleic acid which is adapted to block expression of a gene (for example, asRNA (antisense RNA), siRNA (small interfering RNA), CRISPR (Clustered Regularly Interspaced Short Palindromic Repeats)); reducing or inhibiting a protein which is required for expression or activity of the enzyme by introducing a modification to a gene encoding the protein. It should be appreciated that a protein which is required for expression or activity of the enzyme may act directly on a gene or one or more enzymes, or may act indirectly via another compound. Similarly, a protein which reduces or inhibits the activity or expression of the enzyme may act directly on the gene of the enzyme, or may act indirectly via another compound.

A "genetic modification" should be taken broadly and is intended to include, for example, introducing one or more exogenous nucleic acids to a microorganism, introducing a mutation to a genetic site, adding to or removing from the genome one or more nucleotides, substitution of one or more nucleotides with different nucleotides, substitution of a gene, removal of a gene, addition of a gene and the like.

Meso-2,3-butanediol includes (R,S)- and (S,R)-2,3-butanediol. (R,R)-2,3-butanediol is D-(−)-2,3-butanediol. (S,S)-2,3-butanediol is L-(+)-2,3-butanediol. (R)-Acetoin is D-Acetoin. (S)-Acetoin is L-Acetoin.

Microorganisms

As discussed herein before, the invention provides a recombinant microorganism capable of producing MEK and/or 2-butanol, and optionally one or more other products, by fermentation of a substrate comprising CO.

In one particular embodiment, the microorganism is adapted to express one or more enzymes (or one or more subunits thereof) in the MEK and/or 2-butanol biosynthesis pathway which are not present in a parental microorganism from which it is derived. In another embodiment, the microorganism is adapted to over-express one or more enzymes (or one or more subunits thereof) in the MEK and/or 2-butanol biosynthesis pathway which are present in the parental microorganism. In one embodiment, the microorganism is adapted to express one or more enzymes (or one or more subunits thereof) in the MEK and/or 2-butanol biosynthesis pathways which are not present in a parental microorganism and over-express one or more enzymes (or one or more subunits thereof) in the MEK and/or 2-butanol biosynthesis pathways which are present in a parental microorganism. In one embodiment, the microorganism is adapted to reduce or substantially eliminate the activity of one or more enzymes which are present in a parental microorganism. In one embodiment, the one or more enzymes are a part of the MEK and/or 2-butanol biosynthesis pathways. It should be appreciated that a combination of disrupting the activity of one or more enzymes, over-expressing one or more enzymes and introducing one or more enzymes may be used in the invention.

In one embodiment, the microorganism is adapted to express or overexpress one or more of the following:

an enzyme which catalyses the conversion of (R)-Acetoin to (R,S)-2,3-butanediol;

an enzyme which catalyses the conversion of (R,S)-2,3-butanediol to MEK; and, an enzyme which catalyses the conversion of MEK to 2-butanol.

In one embodiment, the enzyme which catalyses the conversion of (R)-Acetoin to (R,S)-2,3-butanediol is (S)-2,3-butanediol dehydrogenase (EC 1.1.1.B20 or EC1.1.1.76) or a functionally equivalent variant thereof. In one embodiment, the enzyme which catalyses the conversion of (R,S)-2,3-butanediol to MEK is Diol/glycerol dehydratase (EC 4.2.1.28/4.2.1.30) or a functionally equivalent variant thereof. In one embodiment, the enzyme which catalyses the conversion of MEK to 2-butanol is alcohol dehydrogenase (EC 1.1.1.2), or a functionally equivalent variant thereof.

In one embodiment, the microorganism is capable of producing 2-butanol by fermentation of a substrate comprising CO and is adapted to express or overexpress one or more enzymes in the 2-butanol biosynthesis pathway chosen from:

(S)-2,3-butanediol dehydrogenase (EC 1.1.1.B20 or EC1.1.1.76);

Diol/glycerol dehydratase (EC 4.2.1.28/4.2.1.30);

Alcohol dehydrogenase (EC 1.1.1.2); and, a functionally equivalent variant of any one or more thereof.

In one embodiment, the parental microorganism lacks (S)-2,3-butanediol dehydrogenase (EC 1.1.1.B20 or EC1.1.1.76) and Diol/glycerol dehydratase (EC 4.2.1.28/4.2.1.30) or a functionally equivalent variant of any one or more thereof and the recombinant microorganism is adapted to express both these enzymes.

In one embodiment, the parental microorganism comprises (R)-2,3-butanediol dehydrogenase (EC 1.1.1.4) or a functionally equivalent variant thereof and the recombinant microorganism is adapted to reduce or substantially eliminate the activity of this enzyme.

In one embodiment, the microorganism is capable of producing MEK by fermentation of a substrate comprising CO and is adapted to express or overexpress one or more enzymes in the MEK biosynthesis pathway chosen from:

(S)-2,3-butanediol dehydrogenase (EC 1.1.1.B20 or EC1.1.1.76);

Diol/glycerol dehydratase (EC 4.2.1.28/4.2.1.30); and, a functionally equivalent variant of any one or more thereof.

In one embodiment, the parental microorganism lacks (S)-2,3-butanediol dehydrogenase (EC 1.1.1.B20 or EC1.1.1.76) and Diol/glycerol dehydratase (EC 4.2.1.28/4.2.1.30) or a functionally equivalent variant of any one or more thereof and the recombinant microorganism is adapted to express both these enzymes.

In one embodiment, the parental microorganism comprises alcohol dehydrogenase (EC 1.1.1.2) or a functionally equivalent variant thereof and the recombinant microorganism is adapted to reduce or substantially eliminate the activity of this enzyme.

In one embodiment, the parental microorganism comprises (R)-2,3-butanediol dehydrogenase (EC 1.1.1.4) or a functionally equivalent variant thereof and the recombinant microorganism is adapted to reduce or substantially eliminate the activity of this enzyme.

The microorganism may be adapted to express or overexpress the one or more enzymes (or one or more subunits thereof) by any number of recombinant methods including, for example, increasing expression of native genes within the microorganism (for example, by introducing a stronger or constitutive promoter to drive expression of a gene), increasing the copy number of a gene encoding a particular enzyme by introducing exogenous nucleic acids encoding and adapted to express the enzyme, introducing an exogenous nucleic acid encoding and adapted to express an enzyme not present within the parental microorganism.

In certain embodiments, the parental microorganism may be transformed to provide a combination of increased or over-expression of one or more genes native (including naturally present or previously transformed to be present) in the parental microorganism and introduction of one or more genes not native to the parental microorganism. For example, one or more genes encoding one or more enzyme in the MEK and/or 2-butanol biosynthesis pathway may be native to the parental microorganism but it may not include one or more other genes encoding one or more other enzyme in the pathway. The microorganism could for example be engineered to over-express native alcohol dehydrogenase and to introduce one or more nucleic acid encoding one or both enzymes for the conversion of (R)-acetoin to (R,S)-2,3-butanediol and (R,S)-2,3-butanediol to MEK. Skilled persons will appreciate various other combinations of use in the invention.

In a further embodiment, a microorganism of the invention may be further modified from its parent microorganism by introducing a genefit modification which reduces or substantially eliminates the activity of one or both of alcohol dehydrogenase and (R)-2,3-butanediol dehydrogenase. Where the production of MEK is preferred, the reduction of both enzyme activities is preferred. Where the production of 2-butanol is preferred, only (R)-2,3-butanediol dehydrogenase activity is reduced. Reduction or substantially elimination of the activity of (R)-2,3-butanediol dehydrogenase is not essential, but in one embodiment it is preferred.

By way of example only, exemplary amino acid and nucleic acid sequence information for (S)-2,3-butanediol dehydrogenase is provided in the form of H6VRF2 and AFB82681.1 from *Klebsiella pneumoniae.*

By way of example only, exemplary amino acid and nucleic acid sequence information for diol/glycerol dehdratase is provided in tables 1 and 2 below. In certain cases the diol/glycerol dehdratase is vitamin B12 dependent and in others it is B12 independent. Some diol/glycerol dehydratases may get inactivated after catalyzing the reaction and require an activator protein that can reactivate the enzyme by replenishing the co-factor. In certain embodiments, the diol/glycerol dehdratase comprises three subunits (alpha, beta and gamma).

TABLE 1

| B12 independent diol dehydratase | | |
|---|---|---|
| organism | dehydratase | Activator |
| *Clostridium* | ZP_02948838 | ZP_02948836 |
| *butyricum* | NZ_ABDT01000049.2:116638 . . . 119001 | NZ_ABDT01000049.2:115696 . . . 116610 |
| *Clostridium* | AAY34226 | ACF15539 |
| sp. | DQ901409.5:2754 . . . 3668 | AY968605.2:2383 . . . 3297 |
| *Clostridium* | ACI39933 | ACI39932 |
| *diolis* | FJ214109.1:<1 . . . 1920 | FJ214109.1:1947 . . . >2049 |
| *Roseburia* | ZP_03753304 | ZP_03753303 |
| *inulinivorans* | NZ_ACFY01000062.1:43115 . . . 45646 | NZ_ACFY01000062.1:45606 . . . 46457 |

TABLE 2

| B12 dependent diol dehydratase | | | |
|---|---|---|---|
| organism | alpha | beta | Gamma |
| *Klebsiella oxytoca* | 1DIO_A<br>BAA08099.1<br>GI: 868006 | 1DIO_B<br>BAA08100.1<br>GI: 868007 | 1DIO_G<br>BAA08101.1<br>GI: 868008 |
| *Salmonella enterica* | NP_460985<br>GI: 16765370 | NP_460986<br>GI: 16765371 | NP_460987<br>GI: 16765372 |
| *Citobacter koseri* | YP_001452384<br>GI: 157145065 | YP_001452383<br>GI: 157145064 | YP_001452382<br>GI: 157145063 |
| *Klebsiella pneumoniae* | YP_002236782<br>GI: 206575748 | YP_002236781<br>GI: 206575747 | YP_002236780<br>GI: 206575746 |
| *Escherichia coli* | YP_001463342<br>GI: 157157290 | YP_001463343<br>GI: 157157291 | YP_001463344<br>GI: 157157292 |

By way of example only, exemplary amino acid and nucleic acid sequence information for alcohol dehydrogenase is provided in the form of P25984.2, and P14941 and AF157307.2, and X6484. By way of further example, an alcohol dehydrogeanse as described in PCT/NZ2012/000022 could be used.

The references above to sequence information for the various enzymes are GenBank and/or NCBI database references. The sequence information can be readily accessed on-line using these reference numbers.

The enzymes (and any corresponding genes encoding them) of use in the microorganisms of the invention may be derived from any appropriate source, including different genera and species of bacteria, or other organisms. However, in one embodiment, the (S)-2,3-butanediol dehydrogenase is that derived from *Klebsiella pneumonia, Enterobacter aerogenes*, or *Paenibacillus polymyxa*. In one embodiment, the (S)-2,3-butanediol dehydrogenase has the amino acid sequence exemplified above, or it is a functionally equivalent variant thereof. In one embodiment, the diol/glycerol dehdratase is diol dehydratase from *Klebsiella oxytoca*. In one embodiment, the diol/glycerol dehdratase has the amino acid sequence exemplified herein before, or it is a functionally equivalent variant thereof. In one embodiment, the alcohol dehydrogenase is from *Clostridium autoethanogenum*. In one embodiment, the alcohol dehydrogenase has the amino acid sequence exemplified herein before, or it is a functionally equivalent variant thereof.

In the invention, the activity of (R)-2,3-butanediol dehydrogenase is optionally reduced or substantially eliminated. To this extent, the gene and enzyme are those contained in the parental microorganism. Exemplary sequence information for this enzyme includes AEI90715 and HQ876009 from *C. autoethanogenum*, YP_003780482.1 and GI:300855498 from *C. ljungdahlii*, and AEI90716 and HQ876010 from *C. ragsdalei*.

In one embodiment, the microorganism comprises one or more exogenous nucleic acids adapted to increase expression of one or more nucleic acids present in the parental microorganism and which one or more nucleic acids encode one or more of the enzymes (or one or more subunits thereof) referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or Phosphotransacetylase/Acetate kinase operon promoters. It will be appreciated by those of skill in the art that other promoters which can direct expression, preferably a high level of expression under appropriate fermentation conditions, would be effective as alternatives to the exemplified embodiments.

In one embodiment, the microorganism comprises one or more exogenous nucleic acids encoding and adapted to express one or more of the enzymes (or one or more subunits thereof) referred to herein before which are not present in the parental microorganism. In one embodiment, the microorganisms comprise one or more exogenous nucleic acid encoding and adapted to express at least two or three of the enzymes (or one or more subunits thereof).

In one particular embodiment, the microorganism is capable of producing 2-butanol and comprises one or more exogenous nucleic acids encoding one or preferably both of (S)-2,3-butanediol dehydrogenase and diol/glycerol dehydratase, or a functionally equivalent variant of any one or more thereof. A diol/glycerol dehydratase may be comprised of 3 subunits, with each subunit encoded by a different gene. These genes may be combined in a single nucleic acid or two or more nucleic acids which together encode the whole enzyme. In addition, a particular parental microorganism may contain genes for only one, two, or three of these subunits. Accordingly, the invention encompasses engineering the microorganism using one or more exogenous nucleic to express one or two of the subunits only. In one embodiment, the microorganism also comprises one or more nucleic adapted to increase expression of an alcohol dehydrogenase present in the parental microorganism.

In one particular embodiment, the microorganism is capable of producing MEK and comprises one or more exogenous nucleic acids encoding one or preferably both of (S)-2,3-butanediol dehydrogenase and diol/glycerol dehydratase, or a functionally equivalent variant of any one or more thereof. A diol/glycerol dehydratase may be comprised of 3 subunits, with each subunit encoded by a different gene. These genes may be combined in a single nucleic acid or two or more nucleic acids which together encode the whole enzyme. In addition, a particular parental microorganism may contain genes for only one, two, or three of these subunits. Accordingly, the invention encompasses engineering the microorganism using one or more exogenous nucleic to express one or two of the subunits only. In one embodiment, the microorganism also comprises one or more nucleic or genetic modification adapted to reduce or substantially eliminate the conversion of MEK to 2-butanol in the parental microorganism. In one embodiment, the microorganism comprises one or more nucleic acid or genetic modification adapted to reduce or substantially eliminate the activity of alcohol dehydrogenase present in the parental microorganism.

In one embodiment, the (S)-2,3-butanediol dehydrogenase is encoded by a nucleic acid comprising a sequence as herein before exemplified or a functionally equivalent variant thereof. In one embodiment, diol/glycerol dehydratase is encoded by one or more nucleic acid comprising as herein before exemplified, or a functionally equivalent variant of any one or more thereof. In one embodiment, the alcohol dehydrogenase is encoded by one or more nucleic acid comprising as herein before exemplified, or a functionally equivalent variant of any one or more thereof. Alternatively, the enzymes may be encoded by a nucleic acid sequence as described in a publicly available database, for example, as listed herein before.

In one embodiment, where the microorganism is capable of producing either or both MEK and 2-butanol, it is optionally adapted to reduce or substantially eliminate the conversion of (R)-acetoin to (R,R)-2,3-butanediol in the parental microorganism. In one embodiment, the microorganism comprises one or more nucleic acid or genetic modification adapted to reduce or substantially eliminate the activity of (R)-2,3-butanediol dehydrogenase in the parental microorganism.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination.

The exogenous nucleic acids may remain extra-chromosomal upon transformation of the parental microorganism or may integrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

By way of general example, in the case of introducing a genetic modification into a gene, or otherwise disrupting or knocking out a gene or protein, an appropriate nucleic acid construct or vector can be designed to integrate into the genome of the parental microorganism to disrupt a gene. Such constructs will typically include nucleic acid sequences (arms) homologous to a region within or flanking the gene to be disrupted, which allow for homologous recombination to occur, and the introduction of a mutation, the excision of a region of nucleic acid from the gene, or the substitution of a region of the gene with a nucleic acid on the contrast, to occur. While it is preferred that the arms on the constructs have 100% complementarity to the region in the genome which they are targeted to, this is not necessary, provided that the sequence is sufficiently complementary to allow for targeted recombination with the genetic region of interest. Typically, the arms will have a level of homology which would allow for hybridisation to a target region under stringent conditions, as defined in Sambrook et al 1989.

Skilled persons will appreciate nucleic acid sequences sufficient to allow for targeted homologous recombination and integration of an exogenous nucleic acid into the genome of a parental microorganism having regard to the available sequence information for the enzymes referred to herein, particularly alcohol dehydrogenase and (R)-2,3-butanediol dehydrogenase.

In one embodiment, the exogenous nucleic acids encoding one or enzymes (or one or more subunits thereof) as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

In one embodiment, the parental microorganism is selected from the group of carboxydotrophic acetogenic bacteria. In certain embodiments the microorganism is selected from the group comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii*, and *Thermoanaerobacter kiuvi*.

In one particular embodiment, the parental microorganism is selected from the cluster of ethanologenic, acetogenic Clostridia comprising the species *C. autoethanogenum, C. ljungdahlii*, and *C. ragsdalei* and related isolates. These include but are not limited to strains *C. autoethanogenum* JAI-$1^T$ (DSM10061) [Abrini J, Naveau H, Nyns E-J: *Clostridium autoethanogenum*, sp. nov., an anaerobic bacterium that produces ethanol from carbon monoxide. Arch Microbiol 1994, 4: 345-351], *C. autoethanogenum* LBS1560 (DSM19630) [Simpson S D, Forster R L, Tran P T, Rowe M J, Warner I L: Novel bacteria and methods thereof. International patent 2009, WO/2009/064200], *C. autoethanogenum* LBS1561 (DSM23693), *C. ljungdahlii* $PETC^T$ (DSM13528=ATCC 55383) [Tanner R S, Miller L M, Yang D: *Clostridium ljungdahlii* sp. nov., an Acetogenic Species in Clostridial rRNA Homology Group I. Int J Syst Bacteriol 1993, 43: 232-236], *C. ljungdahlii* ERI-2 (ATCC 55380) [Gaddy J L: *Clostridium* stain which produces acetic acid from waste gases. 1997, U.S. Pat. No. 5,593,886], *C. ljungdahlii* C-01 (ATCC 55988) [Gaddy J L, Clausen E C, Ko C-W: Microbial process for the preparation of acetic acid as well as solvent for its extraction from the fermentation broth. 2002, U.S. Pat. No. 6,368,819], *C. ljungdahlii* 0-52 (ATCC 55989) [Gaddy J L, Clausen E C, Ko C-W: Microbial process for the preparation of acetic acid as well as solvent for its extraction from the fermentation broth. 2002, U.S. Pat. No. 6,368,819], *C. ragsdalei* $P11^T$ (ATCC BAA-622) [Huhnke R L, Lewis R S, Tanner R S: Isolation and Characterization of novel Clostridial Species. International patent 2008, WO 2008/028055], related isolates such as "*C. coskatii*" [Zahn et al—Novel ethanologenic species *Clostridium coskatii* (US Patent Application number US20110229947)] and "*Clostridium* sp." (Tyurin et al., 2012, *J. Biotech Res.* 4: 1-12), or mutated strains such as *C. ljungdahlii* OTA-1 (Tirado-Acevedo O. Production of Bioethanol from Synthesis Gas Using *Clostridium ljungdahlii*. PhD thesis, North Carolina State University, 2010). These strains form a subcluster within the Clostridial rRNA cluster I, and their 16S rRNA gene is more than 99% identical with a similar low GC content of around 30%. However, DNA-DNA reassociation and DNA fingerprinting experiments showed that these strains belong to distinct species [Huhnke R L, Lewis R S, Tanner R S: Isolation and Characterization of novel *Clostridial* Species. International patent 2008, WO 2008/028055].

All species of this cluster have a similar morphology and size (logarithmic growing cells are between 0.5-0.7×3-5 μm), are mesophilic (optimal growth temperature between 30-37° C.) and strictly anaerobe [Tanner R S, Miller L M, Yang D: *Clostridium ljungdahlii* sp. nov., an Acetogenic Species in Clostridial rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel *Clostridial* Species. International patent 2008, WO 2008/028055]. Moreover, they all share the same major phylogenetic traits, such as same pH range (pH 4-7.5, with an optimal initial pH of 5.5-6), strong autotrophic growth on CO containing gases with similar growth rates, and a similar metabolic profile with ethanol and acetic acid as main fermentation end product, and small amounts of 2,3-butanediol and lactic acid formed under certain conditions. [Tanner R S, Miller L M, Yang D: *Clostridium ljungdahlii* sp. nov., an Acetogenic Species in *Clostridial* rRNA Homology Group I. Int J Syst Bacteriol 1993, 43: 232-236; Abrini J, Naveau H, Nyns E-J: *Clostridium autoethanogenum*, sp. nov., an anaerobic bacterium that produces ethanol from carbon monoxide. Arch Microbiol 1994, 4: 345-351; Huhnke R L, Lewis R S, Tanner R S: Isolation and Characterization of novel *Clostridial* Species. International patent 2008, WO 2008/028055]. Indole production was observed with all three species as well. However, the species differentiate in substrate utilization of various sugars (e.g., rhamnose, arabinose), acids (e.g., gluconate, citrate), amino acids (e.g., arginine, histidine), or other substrates (e.g., betaine, butanol). Moreover some of the species were found to be auxotroph to certain vitamins (e.g., thiamine, biotin) while others were not.

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

In one embodiment, the parental microorganism lacks the activity of one or more of the following:

an enzyme which catalyses the conversion of (R)-Acetoin to (R,S)-2,3-butanediol;

an enzyme which catalyses the conversion of (R,S)-2,3-butanediol to MEK; and, an enzyme which catalyses the conversion of MEK to 2-butanol.

In one embodiment, the parental microorganism lacks one or more genes encoding one or more of the following:

an enzyme which catalyses the conversion of (R)-Acetoin to (R,S)-2,3-butanediol;

an enzyme which catalyses the conversion of (R,S)-2,3-butanediol to MEK; and, an enzyme which catalyses the conversion of MEK to 2-butanol.

In one embodiment, the parental microorganism lacks one or more genes encoding (S)-2,3-butanediol dehydrogenase, Diol/glycerol dehydratase, and/or alcohol dehydrogenase, and a functionally equivalent variant of any one or more thereof.

In one embodiment, the parental microorganism comprises one or more genes encoding (R)-2,3-butanediol dehydrogenase, alcohol dehydrogenase, and/or a functionally equivalent variant of any one or more thereof.

In one embodiment, the parental microorganism comprises one or more genes encoding encoding (R)-2,3-butanediol dehydrogenase, alcohol dehydrogenase, and/or a functionally equivalent variant of any one or more thereof and lacks one or more genes encoding (S)-2,3-butanediol dehydrogenase, Diol/glycerol dehydratase and/or a functionally equivalent variant of any one or more thereof.

Nucleic Acids

The invention also provides nucleic acids and nucleic acid constructs of use in generating a recombinant microorganism of the invention.

In one embodiment, the nucleic acids comprise one or more sequences encoding one or more of the enzymes (or one or more subunits thereof) in the MEK and/or 2-butanol biosynthesis pathway which when expressed in a microorganism allows the microorganism to produce MEK and/or 2-butanol by fermentation of substrate comprising CO. In one particular embodiment, the invention provides a nucleic acid encoding two or more enzymes (or one or more subunits thereof) which when expressed in a microorganism allows the microorganism to produce MEK and/or 2-butanol by fermentation of substrate comprising CO. In another embodiment, the invention provides a nucleic acid encoding three of said enzymes.

In one particular embodiment, the enzymes are chosen from those enzymes described herein before.

In one embodiment, a nucleic acid of the invention comprises one or more nucleic acid sequences encoding (S)-2,3-butanediol dehydrogenase and diol/glycerol dehydratase and/or a functionally equivalent variant of any one or more thereof, in any order. In one embodiment, the nucleic acid further comprises one or more nucleic acid sequences encoding alcohol dehydrogenase.

Exemplary amino acid sequences and nucleic acid sequence encoding each of the above enzymes are provided herein or can be obtained from GenBank as mentioned hereinbefore. However, skilled persons will readily appreciate alternative nucleic acids sequences encoding the enzymes or functionally equivalent variants thereof, having regard to the information contained herein, in GenBank and other databases, and the genetic code.

In one embodiment, a nucleic acid encoding (S)-2,3-butanediol dehydrogenase has a sequence as herein before described or is a functionally equivalent variant thereof.

In one embodiment, the nucleic acid sequence encoding diol/glycerol dehydratase has a sequence as herein before described or is a functionally equivalent variant thereof.

In one embodiment, the nucleic acid sequence encoding alcohol dehydrogenase has a sequence as herein before described or is a functionally equivalent variant thereof.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kindase promoter is used. In another embodiment a pyruvate:ferredoxin oxidoreductase promoter, an Rnf complex operon promoter or an ATP synthase operon promoter. In one particular embodiment, the promoter is from *C. autoethanogenum.*

The nucleic acids of the invention may remain extrachromosomal upon transformation of a parental microorganism or may be adapted for intergration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, protoplast transformation, chemical or natural competence, prophage induction or conjugation. Suitable transformation techniques are described for example in, Sambrook J, Fritsch E F, Maniatis T: Molecular Cloning: A laboratory Manual, Cold Spring Harbour Labrotary Press, Cold Spring Harbour, 1989.

Electroporation has been described for several carboxydotrophic acetogens as *C. ljungdahlii* (Köpke et al. 2010, *Poc. Nat. Acad. Sci. U.S.A.* 107: 13087-92; PCT/NZ2011/000203; WO2012/053905), *C. autoethanogenum* (PCT/NZ2011/000203; WO2012/053905), or *Acetobacterium woodii* (Straetz et al., 1994, *Appl. Environ. Microbiol.* 60:1033-37) and is a standard method used in many Clostridia such as *C. acetobutylicum* (Mermelstein et al., 1992, *Biotechnology*, 10, 190-195), *C. cellulolyticum* (Jennert et al., 2000, *Microbiology*, 146: 3071-3080) or *C. thermocellum* (Tyurin et al., 2004, *Appl. Environ. Microbiol.* 70: 883-890). Prophage induction has been demonstrated for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University), while conjugation has been described as method of choice for many Clostridia including *Clostridium difficile* (Herbert et al., 2003, *FEMS Microbiol. Lett.* 229: 103-110) or *C. acetobuylicum* (Williams et al., 1990, *J. Gen. Microbiol.* 136: 819-826) and could be used in a similar fashion for carboxydotrophic acetogens. *E. coli* donor strains such as *E. coli* HB101 with plasmid R702 may be used (Williams et al., 1990, *J. Gen. Microbiol.* 136: 819-826).

In certain embodiments, due to the restriction systems which are active in the microorganism to be transformed, it is necessary to methylate the nucleic acid to be introduced into the microorganism. This can be done using a variety of techniques, including those described below.

By way of example, in one embodiment, a recombinant microorganism of the invention is produced by a method comprising the following steps:

introduction into a shuttle microorganism of (i) of an expression construct/vector as described herein and (ii) a methylation construct/vector comprising a methyltransferase gene;

expression of the methyltransferase gene;

isolation of one or more constructs/vectors from the shuttle microorganism; and, introduction of the one or more construct/vector into a destination microorganism.

In one embodiment, the methyltransferase gene of step B is expressed constitutively. In another embodiment, expression of the methyltransferase gene of step B is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli, Bacillus subtillis*, or *Lactococcus lactis.*

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thio-galactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of a methyltransferase described in PCT/NZ2011/000203 (WO2012/053905), or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase comprises the sequence of a methyltransferase described in PCT/NZ2011/000203 (WO2012/053905), or it is a functionally equivalent variant thereof.

Any number of constructs/vectors adapted to allow expression of a methyltransferase gene may be used to generate the methylation construct/vector.

Methods of Production

The invention provides a method for the production of MEK and/or 2-butanol and optionally one or more other products by microbial fermentation comprising fermenting a substrate comprising CO using a recombinant microorganism of the invention. Preferably, MEK and/or 2-butanol is the main fermentation product. The methods of the invention may be used to reduce the total atmospheric carbon emissions from an industrial process.

Preferably, the fermentation comprises the steps of anaerobically fermenting a substrate in a bioreactor to produce at least MEK and/or 2-butanol using a recombinant microorganism of the invention.

In one embodiment the method comprises the steps of:

(a) providing a substrate comprising CO to a bioreactor containing a culture of one or more microorganism of the invention; and (b) anaerobically fermenting the culture in the bioreactor to produce at least MEK and/or 2-butanol.

In one embodiment the method comprises the steps of:

(a) capturing CO-containing gas produced as a result of the industrial process, before the gas is released into the atmosphere;

(b) the anaerobic fermentation of the CO-containing gas to produce the at least MEK and/or 2-butanol by a culture containing one or more microorganism of the invention.

In one particular embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and gas-to-at least MEK and/or 2-butanol to occur, in addition to the CO-containing substrate gas, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce one or more products using CO are known in the art. For example, suitable media are described Biebel (2001). In one embodiment of the invention the media is as described in the Examples section herein after.

The fermentation should desirably be carried out under appropriate conditions for the gas-to-the at least MEK and/or 2-butanol fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of at least MEK and/or 2-butanol. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO-to-at least MEK and/or 2-butanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e., bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, $O_2$ may reduce the efficiency of an anaerobic fermentation process. Processing of unwanted or unnecessary gases in stages of a fermentation process before or after fermentation can increase the burden on such stages (e.g., where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a microorganism of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

MEK and/or 2-butanol, or a mixed stream containing MEK and/or 2-butanol and/or one or more other products, may be recovered from the fermentation broth by methods known in the art, such as fractional distillation or evaporation, pervaporation, gas stripping and extractive fermentation, including for example, liquid-liquid extraction. By way of further example, methods for the extraction of butanol are described in: Köpke & Dürre, 2011, Biochemical production of biobutanol, In: Handbook of biofuels production: processes and technologies (Eds.: Luque, Campelo & Clark), Woodhead Publishing Ltd, Camebridge, UK: 221-257.

In certain preferred embodiments of the invention, MEK and/or 2-butanol and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.

Microorganisms

*C. autoethanogenum* DSM10061 and DSM23693 (a derivative of DSM10061) as well as *C. ljungdaghlii* DSM13528 were obtained from DSMZ (The German Collection of Microorganisms and Cell Cultures, Inhoffenstraβe 7 B, 38124 Braunschweig, Germany). Growth was carried out at 37° C. using strictly anaerobic conditions and techniques (Hungate, 1969, Methods in Microbiology, vol. 3B. Academic Press, New York: 117-132; Wolfe, 1971, Adv. Microb. Physiol., 6: 107-146). Chemically defined PETC media without yeast extract (Tab. 1) and 30 psi carbon monioxide containing steel mill waste gas (collected from New Zealand Steel site in Glenbrook, NZ; composition: 44% CO, 32% N2, 22% CO2, 2% H2) as sole carbon and energy source was used.

TABLE 3

| PETC medium | |
|---|---|
| Media component | Concentration per 1.0 L of media |
| NH4Cl | 1 g |
| KCl | 0.1 g |

TABLE 3-continued

| PETC medium | |
|---|---|
| Media component | Concentration per 1.0 L of media |
| MgSO4•7H2O | 0.2 g |
| NaCl | 0.8 g |
| KH2PO4 | 0.1 g |
| CaCl2 | 0.02 g |
| Trace metal solution | 10 ml |
| Wolfe's vitamin solution | 10 ml |
| Resazurin (2 g/L stock) | 0.5 ml |
| NaHCO3 | 2 g |
| Reducing agent | 0.006-0.008% (v/v) |
| Distilled water | Up to 1 L, pH 5.5 (adjusted with HCl) |
| Wolfe's vitamin solution | per L of Stock |
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |
| Vitamin B12 | 0.1 mg |
| p-Aminobenzoic acid | 5 mg |
| Lipoic acid | 5 mg |
| Thiamine | 5 mg |
| Distilled water | To 1 L |
| Trace metal solution | per L of stock |
| Nitrilotriacetic Acid | 2 g |
| MnSO4•H2O | 1 g |
| Fe (SO4)2(NH4)2•6H2O | 0.8 g |
| CoCl2•6H2O | 0.2 g |
| ZnSO4•7H2O | 0.2 mg |
| CuCl2.2H2O | 0.02 g |
| NaMoO4•2H2O | 0.02 g |
| Na2SeO3 | 0.02 g |
| NiCl2•6H2O | 0.02 g |
| Na2WO4•2H2O | 0.02 g |
| Distilled water | To 1 L |
| Reducing agent stock | per 100 mL of stock |
| NaOH | 0.9 g |
| Cystein•HCl | 4 g |
| Na2S | 4 g |
| Distilled water | To 100 mL |

Analysis of Metabolites

To remove proteins and other cell residues, 400 μl samples were mixed with 100 μl of a 2% (w/v) 5-Sulfosalicylic acid and centrifuged at 14,000×g for 3 min to separate precipitated residues. 10 μl of the supernatant was then injected into the HPLC for analyses. HPLC analysis of 2,3-butanediol, 2-butanol and other metabolites was performed using an Agilent 1100 Series HPLC system equipped with a RID operated at 35° C. (Refractive Index Detector) and an Aminex HPX-87H column (300×7.8 mm, particle size 9 μm) kept at 35° C. Slightly acidified water was used (0.005 M $H_2SO_4$) as mobile phase with a flow rate of 0.6 ml/min. For distinction of 2,3-butanediol sterioisomers HPLC analysis was performed using an Agilent 1100 Series HPLC system equipped with a RID operated at 35° C. (Refractive Index Detector) and an Alltech IOA-2000 Organic acid column (150×6.5 mm, particle size 8 μm) kept at 60° C. Slightly acidified water was used (0.005 M $H_2SO_4$) as mobile phase with a flow rate of 0.25 ml/min.

Conversion of MEK to 2-Butanol in *C. autoethanogenum* by Alcohol Dehydrogenase

An alcohol dehydrogenase (Adh; EC 1.1.1.2) was identified in genome of carboxydotrophic *C. autoethanogenum* (described in PCT/NZ2012/000022) that is able to convert MEK to 2-butanol. This enzyme has homology to an alcohol dehydrogenase from *C. beijerinckii* described to convert MEK to 2-butanol (Ismail et al., *J. Bacteriol,* 1993, 175: 5079-5105).

To confirm this activity, a growth experiment with carboxydotrophic acetogens *C. autoethanogenum, C. ljungdahlii* and *C. ragsdalei* was carried out in 50 mL serum bottles with PETC medium (Tab. 1) and steel mill waste gas (collected from New Zealand Steel site in Glenbrook, NZ; composition: 44% CO, 32% N2, 22% CO2, 2% H2) as sole carbon and energy source. During logarithmic growth, 5 g/L MEK were added to the culture. At end of growth, no MEK was left, but an equal amount of 2-butanol was detected (Table 4). Enzymes assays were carried out according to Ismail et al. (*J. Bacteriol,* 1993, 175: 5079-5105) with crude extract of *C. autoethanogenum*, and activity could be successfully detected with MEK as substrate and NADPH as co-factor.

TABLE 4

| Conversion of MEK to 2-butanol by carboxydotrophic acetogens *C. autoethanogenum, C. ljungdahlii, C. ragsdalei* | | | |
|---|---|---|---|
| | MEK added | MEK at end of growth | 2-butanol at end of growth |
| *C. autoethanogenum* | 5.0 g/L | 0.1 g/L | 5.0/g/L |
| *C. ljungdahlii* | 5.1 g/L | 0.1 g/L | 4.8 g/L |
| *C. ragsdalei* | 5.3 g/L | 0.3 g/L | 4.4 g/L |

As further proof for activity, the alcohol dehydrogenase gene was cloned into an expression vector, overproduced in *E. coli* and measured for activity converting MEK to 2-butanol.

The gene was amplified from genomic DNA and cloned into a pBAD vector via KpnI and HindIII, with the following recipe. The amplified ADH gene was similarly digested with KpnI-HF and HindIII and transformed into *E. coli* MC1061 cells by electroporation. The sequence of the ADH gene was verified by DNA sequencing. The transformed cells were grown in 100 mL LB with ampicillin at 37° C. until an $OD_{600}$ of 0.8 was reached. At this point, 1 mL of 20% arabinose was added and the culture was incubated at 28° C. for the remainder of the expression. Cells were pelleted, and supernatant decanted. Pellets were then resuspended in HEPES buffer (50 mM Na-HEPES and 0.2 mM DTT, pH 8.0), and 0.2 μL each of Benzonase (Merck, 25 units/μL) and rLysozyme (Merck, 30 kU/μL) were added. The alcohol dehydrogenase was then purified via the fused N-terminal $His_6$tag using immobilized metal affinity chromatography. After a 30 min incubation on ice, the cells were lysed by sonication, insoluble debris was pelleted, and the supernatant was clarified using a 0.2 micron filter. The clarified supernatant was added to Talon resin (Clontech) which had been thoroughly washed with lysis buffer. A bed volume of 500 μL was used for purification and the protein was allowed to bind to the Talon resin for an hour at 4° C. and then washed several times with lysis buffer. The protein was eluted from the column using lysis buffer supplemented with 150 mM imidazole, and the eluant was collected in 500 μL fractions. Aliquots taken at various stages through the purification process, as well as all elution fractions, were run on an SDS PAGE gel to confirm presence of the protein and determine the success of the purification. Proteins were exchanged into a storage buffer (50 mM potassium phosphate, 150 mM NaCl, 10% v/v glycerol, pH 7.0) using Amicon Ultra-4 Centrifugal Filter Units (Millipore). The protein was highly soluble when expressed in *E. coli*, and could be readily purified. The activity assays were carried out in a UV/visspectrophotometer with quartz cuvettes using NADPH as a cofactor in a concentration of 0.2 mM and 3 mM MEK as a substrate. The assay mixture contained 50 mM Tris-HCl buffer (pH 7.5), with 1 mM DTT. The alcohol dehydrogenase showed activity with MEK as substrate, having a $K_{cat}$ of 44±2 $sec^{-1}$, a $K_M$ of 1.2±0.1 mM and a resulting Kcat/$K_M$ of $3.8\times10^4$ $sec^{-1}$ $mM^{-1}$.

Construction of *Clostridium* Expression Plasmid with Diol Dehydratase Genes (pddABC) from *Klebsiella oxytoca*

Standard Recombinant DNA and molecular cloning techniques were used [Sambrook J, Fritsch E F, Maniatis T: Molecular Cloning: A laboratory Manual, Cold Spring Harbour Labrotary Press, Cold Spring Harbour, 1989; Ausubel F M, Brent R, Kingston R E, Moore D D, Seidman J G, Smith J A, Struhl K: *Current protocols in molecular biology*. John Wiley & Sons, Ltd., Hoboken, 1987].

The promoter region of the phosphotransacetylase-acetate kinase operon (Ppta-ack) (SEQ ID NO: 1) was amplified from genomic DNA of *C. autoethanogenum* DSM10061 using primers Ppta-ack-NotI-F (SEQ ID NO: 2: GAGCGGCCGCAATATGATATTTATGTCC) and Ppta-ack-NdeI-R (SEQ ID NO: 3: TTCCATATGTTTCATGTTCATTTCCTCC) and cloned into the *E. coli-Clostridium* shuttle vector pMTL83151 (FJ797647.1; Nigel Minton, University of Nottingham, UK) [Heap J T, Pennington O J, Cartman S T, Minton N P. A modular system for *Clostridium* shuttle plasmids. *J Microbiol Methods*. 2009, 78: 79-85] using NotI and NdeI restriction sites, generating the plasmid pMTL83155.

Genomic DNA from *Clostridium autoethanogenum* DSM 10061 was isolated using a modified method by Bertram and Dürre (1989). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 μl lysozyme (100,000 U) were added and the mixture was incubated at 37° C. for 30 min, followed by addition of 280 μl of a 10% (w/v) SDS solution and another incubation for 10 min. RNA was digested at room temperature by addition of 240 μl of an EDTA solution (0.5 M, pH 8), 20 μl Tris-HCl (1 M, pH 7.5), and 10 μl RNase A (Fermentas). Then, 100 μl Proteinase K (0.5 U) were added and proteolysis took place for 1-3 h at 37° C. Finally, 600 μl of sodium perchlorate (5 M) were added, followed by a phenol-chloroform extraction and an isopropanol precipitation. DNA quantity and quality was inspected spectrophotometrically.

The genes encoding the diol dehydratase (EC 4.2.1.28, Accession D45071) from *Klebsiella oxytoca*, pddABC, were synthesized in a single operon with codons optimised for *Clostridium autoethanogenum* (SEQ ID NO: 4) flanked by NdeI and EcoRI restriction sites for further sub-cloning. The pddABC operon was then sub-cloned from the pUC57 vector into the pMTL83155 using restriction enzymes NdeI and EcoRI.

Introduction of pddABC Expression Plasmid into *C. autoethanogenum*

The plasmid, pMTL83155-pddABC was used to transform *C. autoethanogenum* using methods described above. Outgrowth was performed on YTF-agar (8 g/L tryptone, 5 g/L yeast extract, 2 g/L NaCl, 2.5 g/L fructose, and 7.5 g/L agar, pH 5.8) containing 15 μg $mL^{-1}$ thiamphenicol, and incubated at 37° C. in 30 psi Real Mill Gas. Single colonies were restreaked on PETC-MES-agar (Tab. 1, with MES instead of carbonate buffer and without fructose) containing 15 μg $mL^{-1}$ thiamphenicol, then restreaked on PETC-MES-agar containing 15 μg $mL^{-1}$ thiamphenicol and 0.5% fructose. Multiple colonies were picked up from the plates with fructose and grown up in 3 mL of PETC-MES with 0.5% fructose in Balch tubes with 30 psi Real Mill Gas. Presence of plasmid was verified by PCR.

Testing in Vivo Activity of Diol Dehydratase in *C. autoethanogenum*

The strain of *C. autoethanogenum* harbouring pMTL83155-pddABC was grown in the presence of meso-2,3-butanediol and compared to the wild-type as a control. When the growth medium was supplemented with 5 g $L^{-1}$ meso-2,3-butanediol, after 92 hrs of growth 12 mg $L^{-1}$2-butanol was detected in the culture of the transformed strain while none was detected in the wild-type (Table 5). Without being bound to theory, the authors believe that the diol dehydratase converts meso-23BDO to MEK, while alcohol dehydrogenase activity present in *C. autoethanogenum* as described above then converts MEK to 2-butanol.

TABLE 5

Key metabolites from *C. autoethanogenum* with and without pddABC genes expressed in the presence and absence of meso-2,3-butanediol. Values represent the mean plus or minus one standard deviation of three replicates.

| Sample | Acetic acid (g $L^{-1}$) | Ethanol (g $L^{-1}$) | 2-butanol (mg $L^{-1}$) |
|---|---|---|---|
| *C. autoethanogenum* harbouring pddABC + meso-2,3-butanediol | 2.97 ± 0.15 | 1.33 ± 0.06 | 12.33 ± 1.53 |
| *C. autoethanogenum* harbouring pddABC | 3.00 ± 0.00 | 1.47 ± 0.06 | ND |
| *C. autoethanogenum* wild-type + meso-2,3-butanediol | 2.67 ± 0.06 | 0.97 ± 0.06 | ND |
| *C. autoethanogenum* wild-type | 3.07 ± 0.72 | 1.17 ± 0.06 | ND |

Improvement of Meso-BDO to MEK Conversion by Co-Expression of Reactivator Proteins ddrAB The reaction of diol dehydratase PddABC enzyme complex with 2,3-butanediol, while leading to product formation, can also lead to inactivation of the enzyme complex (Bachovin et. al. 1977). In the native organism as *K. oxytoca* additional enzymes exist which are able to reactivate the damaged enzyme complex (Mori K. et al, 1997). To improve the efficiency of conversion of meso-2,3-butanediol to MEK, the appropriate reactivator proteins (YP_005016278 and) are coexpressed with the diol dehydratase genes. The reactivator protein genes (GeneID:11660428 and), ddrAB, from *K. oxytoca* are synthesized with codons optimised for *C. autoethanogenum* (SEQ ID NO: 6) flanked by restriction sites SacI and KpnI. The ddrAB operon is cloned into pMTL83155-pddABC with resctiction enzymes SacI and KpnI. The generated vector, pMTL83155-pddABC-ddrAB, is used to transform *C. autoethanogenum* as described above to improve conversion of meso-2,3-butanediol to MEK and 2-butanol.

Construction of Expression Plasmid with Genes for Production of meso-2,3-butanediol and In Vivo Test in *E. coli*

Figure 2:
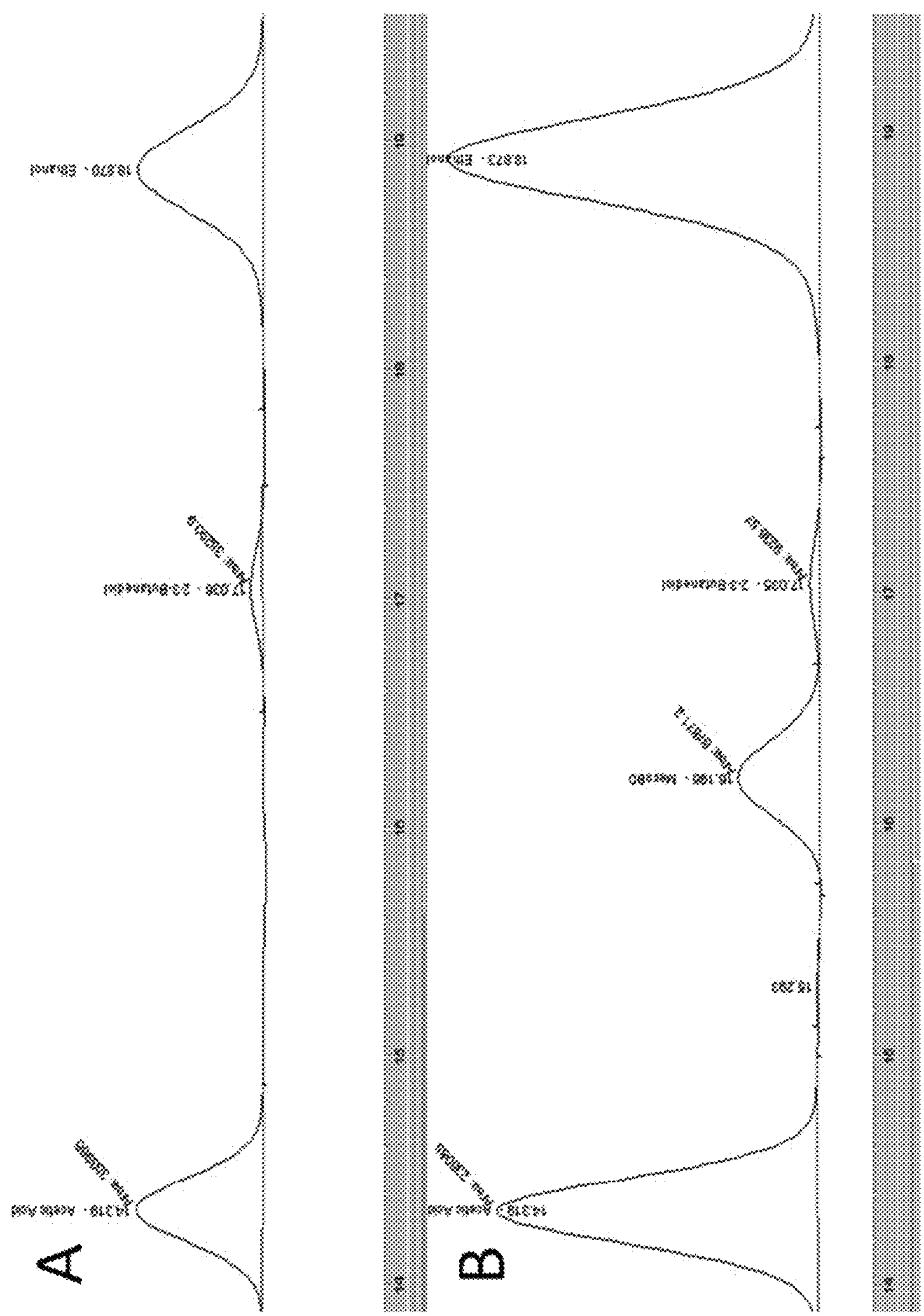
FIG. 2: HPLC profiles highlighting butanediol production in transformed *E. coli* JW1375. Note: Y-axis is not scaled equally between the graphs. The four peaks visible are acetic acid at 14.3 min, meso-2,3-butanediol at 16.2 min, (D,L)-2,3-butanediol at 17.0 min, and ethanol at 18.9 min. A. Shows the profile of JW1375 with pMTL85145-ALS-ALDC-secAdh593, with no detected meso-2,3-butanediol, and some (D)-2,3-butanediol. B. Shows the profile of JW1375 with pMTL85145-ALS-ALDC-$_{Kp}$budC, with meso-2,3-butanediol produced along with some (D)-2,3-butanediol.

In the interest of producing meso-2,3-butanediol in *C. autoethanogenum* the inventors identified budC (EC 1.1.1.303, Accession YP_001335719) from *Klebsiella pneumoniae* as capable of converting (R)-acetoin, which is present as an intermediate in *C. autoethanogenum*, to meso-2,3-butanediol. This gene was synthesized with codons optimised for *Clostridium autoethanogenum* by (SEQ ID NO: 5) and received in the cloning vector pBSK flanked by SalI and XhoI restriction sites for further sub-cloning. The synthesis of acetoin from pyruvate requires the successive actions of acetolactate synthase (ALS) and acetolactate decarboxylase (ALDC), so a plasmid that constitutes these two genes was constructed. First, the promoter region of the phosphotransacetylase-acetate kinase operon (Ppta-ack) (SEQ ID NO: 1) was amplified from genomic DNA of *C. autoethanogenum* DSM10061 using primers Ppta-ack-NotI-F (SEQ ID NO: 2: GAGCGGCCGCAATATGATATTTATGTCC) and Ppta-ack-NdeI-R (SEQ ID NO: 3: TTCCATATGTTTCATGTTCATTTCCTCC) and cloned into the *E. coli-Clostridium* shuttle vector pMTL85141 (FJ797651.1; Nigel Minton, University of Nottingham, UK) [Heap J T, Pennington O J, Cartman S T, Minton N P. A modular system for *Clostridium* shuttle plasmids. *J Microbiol Methods*. 2009, 78: 79-85] using NotI and NdeI restriction sites, generating the plasmid pMTL85145. Following that, the gene als from *C. autoethanogenum* was amplified using primers als-NdeI-F (SEQ ID NO: 7: GGAAGTTTCATATGAATAGAGATAT) and als-EcoR1-R (SEQ ID NO: 8: GGTATAGAATTCTGGTTTAATAGATAATGC), and the resulting amplicon was cloned into pMTL85145 using NdeI and EcoRI restriction sites. ALDC was then added into this plasmid by amplification using primers ALDC-EcoR1-F (SEQ ID NO:9: GCGAATTCGACATAGAGGTGAATGTAATATGG) and ALDC-SacI-R (SEQ ID NO: 10: GCGAGCTCTTATTTTTCAACACTTGTTATCTCA) and then cloning using restriction sites EcoR1 and SacI, generating plasmid pMTL85145-ALS-ALDC. The budC gene was cloned into pMTL85145-ALS-ALDC. This construct was used to transform *E. coli* JW1375-1 (ldhA744(del)::kan) obtained from Genetic Coli Stock Centre (GCSC). The resulting strain was grown anaerobically in M9 medium with 2% glucose, with a strain harbouring pMTL85145-ALS-ALDC-secAdh593 as a control. The control strain produced (D)-(−)-2,3-butanediol, and no detectable meso-2,3-butanediol (FIG. 2). The strain harbouring the construct with budC produced 310 mg $L^{-1}$ meso-(R,S)-2,3-butanediol and a small amount of (D)-(R,R)-2,3-butanediol (FIG. 2).

Production of Meso-BDO from Carbon Monoxide

Inactivation of D-(−)-2,3-butanediol dehydrogenase of *C. autoethanogenum* DSM23693:

2,3-butanediol dehydrogenase (2,3-bdh) gene involved in D-(−)-2,3-BDO production in *C. autoethanogenum* DSM23693 was inactivated using ClosTron group II intron mediated gene disruption tool (Heap et al., 2010). The Perutka algorithm hosted at ClosTron.com was used to identify the group II intron target site between bases 468 and 469 on the sense strand of 2,3-bdh gene that have been synthesized and delivered in pMTL007C-E5 vector. The final vector pMTL007C-E5-2,3bdh-468!469s (SEQ ID NO: 11), contain a Retro-transposition-Activated ermB Marker (RAM) which confers resistance to antibiotic Clarithromycin upon insertion into the target site.

The pMTL007C-E5-2,3bdh-468!469s plasmid was introduced into *C. autoethanogenum* DSM23693 as described above. Streaks of single colonies were made sequentially first on PETC-MES media containing 15 μg/ml thiamphenicol followed by on agar plates with PETC-MES media containing 5 μg/ml Clarithromycin. 4 colonies per plasmid were randomly screened for group II intron insertion by PCR using primers Og42f (SEQ ID NO: 12) and Og43r (SEQ ID NO: 13), flanking the group II intron insertion site in 2,3-bdh gene. The Maxime PCR PreMix Kit was used for PCR. 16s rDNA was also PCR amplified using primers fD1 (SEQ ID NO: 14) and rP2 (SEQ ID NO: 15) and Maxime PCR PreMix Kit.

Figure 3:
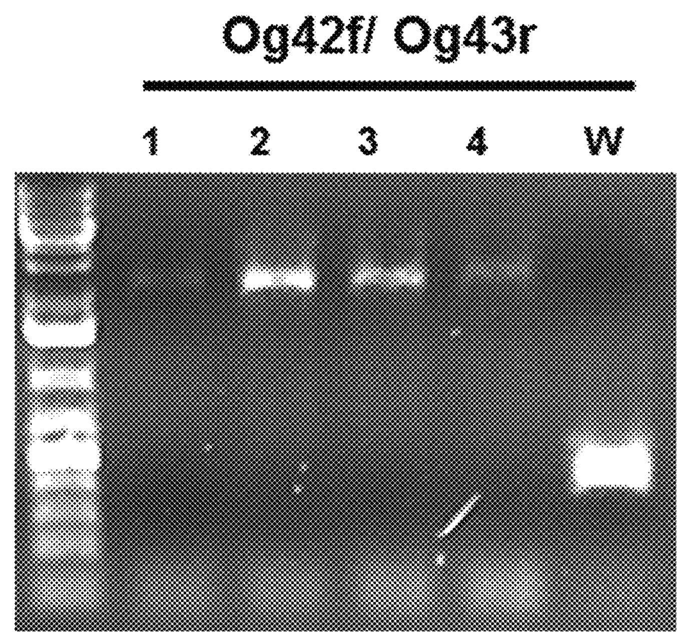
FIG. 3: Confirmation of amplification of 2,3bdh gene disruption in 4 clones. PCR products of 375 bp with primers Og42f/Of43r indicates the unmodified wild type 2,3-bdh gene (W). Amplification of PCR products of ~2 kb using the same set of primers indicates insertion of ClosTron group II intron in the target gene. All 4 clones which were targeted for 2,3-bdh gene are positive for gene disruption as seen by the amplification of ~2 kb PCR product (1-4).

Confirmation of 2,3bdh Gene Disruption:

Amplification of PCR products of 375 bp with primers Og42f/Of43r indicates the unmodified wild type 2,3-bdh gene. Amplification of PCR products of ~2 kb using the same set of primers indicates insertion of ClosTron group II intron in the target gene. All 4 clones which were targeted for 2,3-bdh gene are positive for gene disruption as seen by the amplification of ~2 kb PCR product (FIG. 3). These results confirm the disruption of 2,3-bdh genes in *C. autoethanogenum* DSM23693.

Expression of meso-2,3-butanediol Producing Dehydrogenase

Construction of Expression Vector:

In the interest of producing meso-2,3-butanediol in *C. autoethanogenum* the inventors identified budC (EC 1.1.1.303, Accession YP_001335719) from *K. pneumoniae* as capable of converting (R)-acetoin, which is present as an intermediate in *C. autoethanogenum*, to meso-2,3-butanediol. This gene was synthesized with codons optimised for *Clostridium autoethanogenum* (SEQ ID NO: 5) flanked by NdeI and EcoRI restriction sites for further sub-cloning. First, the promoter region of the phosphotransacetylase-acetate kinase operon (Ppta-ack) was cut from pMTL85145 NotI and NdeI restriction sites and cloned into pMTL83151 (FJ797651.1; Nigel Minton, University of Nottingham, UK) [Heap J T, Pennington O J, Cartman S T, Minton N P. A modular system for *Clostridium* shuttle plasmids. *J Microbiol Methods*. 2009, 78: 79-85] cut with NotI and NdeI, generating pMTL83155. Using restriction sites NdeI and EcoRI, the budC gene from *K. pneumoniae* was cloned into pMTL83155, generating pMTL83155-KpBDH.

Transformation of *C. autoethanogenum:*

To produce meso-2,3-butanediol from CO, the expression plasmid, pMTL83155-KpBDH was used to transform *C. autoethanogenum* DSM23693 and the generated mutant with disrupted2,3-bdh gene using methods described above with thiamphenicol (15 mg $L^{-1}$) selection.

Meso-2,3-butanediol Production in Transformed *C. autoethanogenum:*

Figure 4:
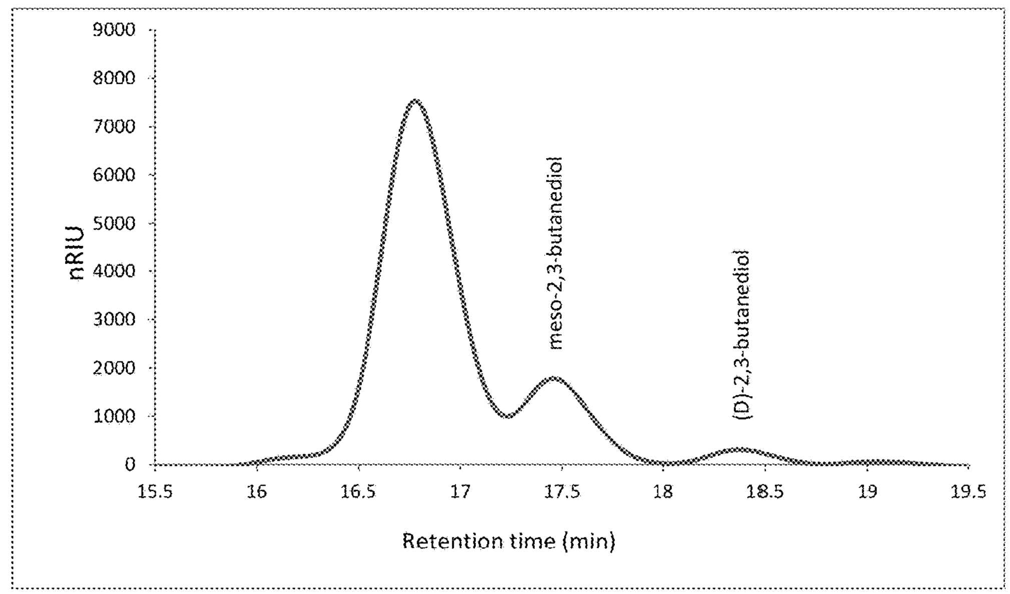
FIG. 4: Confirmation of meso-2,3-butanediol production in 12-well plates by HPLC. Chromatogram shows peaks for meso-2,3-Butanediol and D-(−)-2,3-butanediol. A ratio of 5.4:1 was measured.

To test production of meso-2,3-butanediol, the transformed strains were grown on real mill gas in 2-mL cultures at 2 bar(g). In the background of the mutant with interrupted native 2,3-bdh gene meso-2,3-butanediol was produced, 370±70 mg L-1 (average of nine samples±one standard deviation)(FIG. 4) with a ratio of 5.4:1 of meso-2,3-butanediol to D-(−)-2,3Butanediol. Samples of this growth experiment were analysed by qRT-PCR for expression of the meso-butanediol dehydrogenase gene (see below).

Meso-2,3-butanediol Production in Transformed *C. autoethanogenum* in a Continuous-Stirred Tank Reactor (CSTR):

Approximately 1500 mL of solution A (table 6) was transferred into a 1.5 L fermenter and sparged with nitrogen. Resazurin (1.5 mL of a 2 g/L solution) and H3PO4 (85% solution, 2.25 mL) was added and the pH adjusted to 5.0 using concentrated NH4OH(aq). Nitrilotriacetic acid (0.3 ml of a 0.15M solution) was added prior to 1.5 ml of solution C (table 6). This was followed by NiCl2 (0.75 ml of 0.1M solution) and Na2WO3 (1.5 mL of a 0.01M solution). 15 ml of solution B (table 6) was added and the solution sparged with N2 before switching to CO containing gas (50% CO; 28% N2, 2% H2, 20% CO2) at 50 mL/min. The fermenter was then inoculated with 200 ml of a *Clostridium autoethanogenum* culture with plasmid pMTL83155-KpBDH and a disrupted D-(−)-2,3-bytanediol dehydrogenase gene. The fermenter was maintained at 37° C. and stirred at 200 rpm. During this experiment, Na2S solution (0.2M solution) was added at a rate of approx 0.1 ml/hour. Substrate supply was increased in response to the requirements of the microbial culture.

Figure 5:
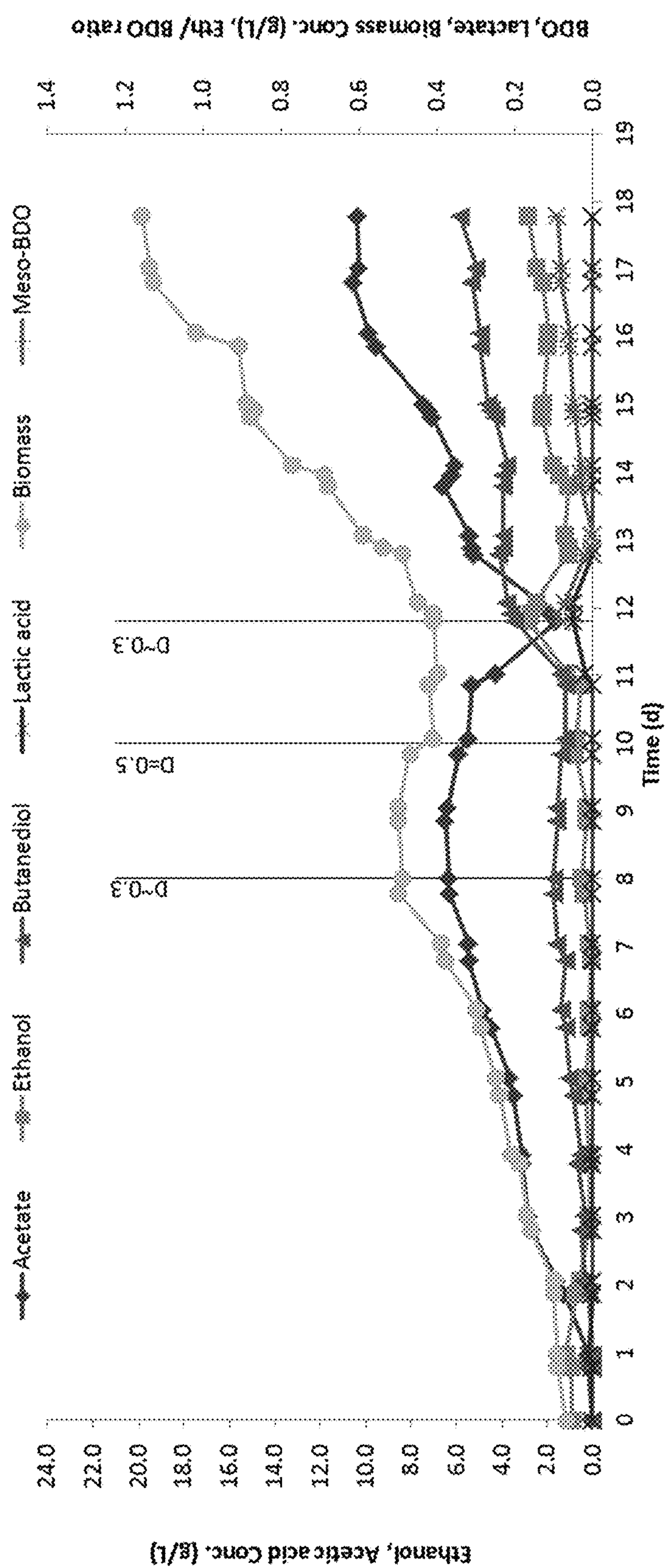
FIG. 5: Metabolite profile for reactor run of *C. autoethanogenum* harbouring plasmid pMTL83155-KpBDH. At selected points, meso-2,3-butanediol was measured and successfully detected.
Figure 6:
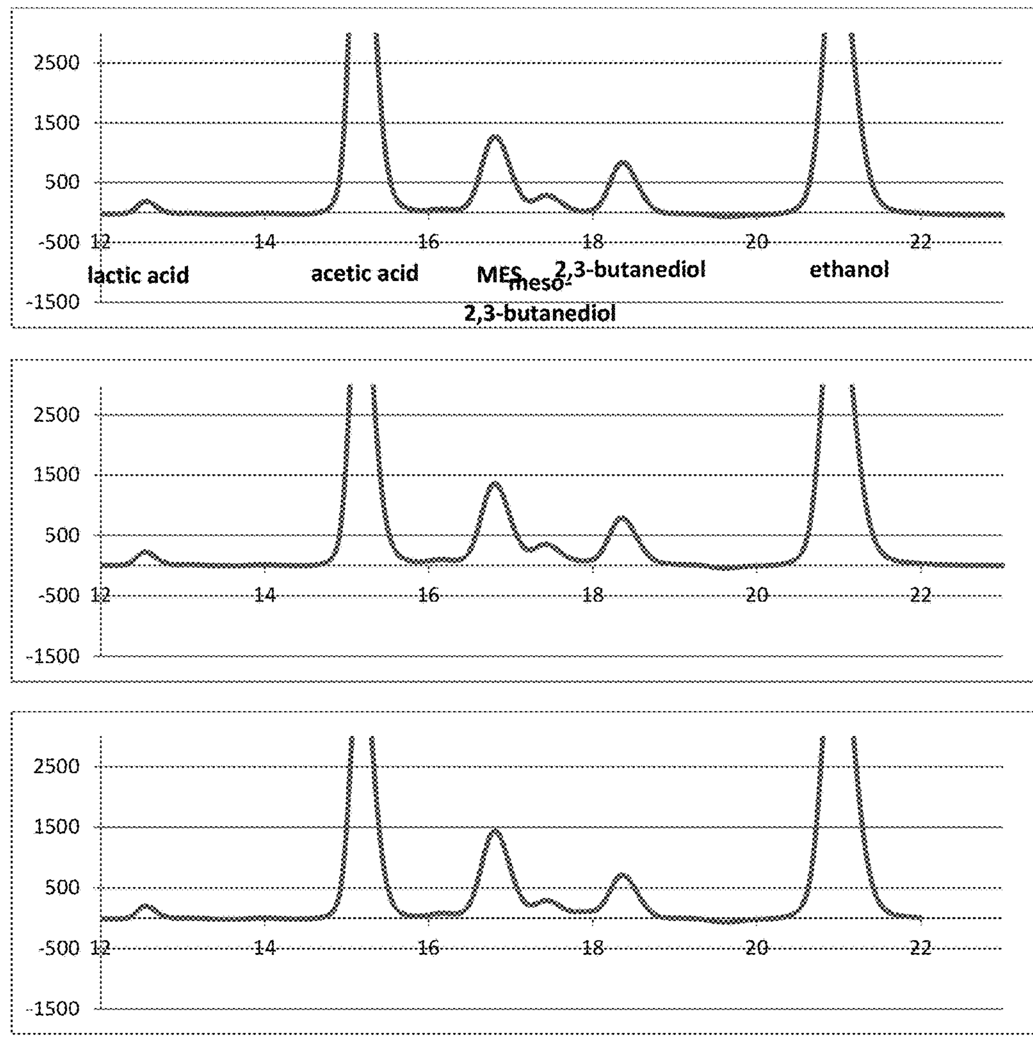
FIG. 6: Confirmation of meso-2,3-butanediol production in 3 samples from continuous culture by HPLC.

A fermentation profile is shown in FIG. 5. Production of meso-BDO was confirmed in continuous fermentation over multiple sampling points at a concentration of 0.2 g/L and a ratio of 1:1 with the D-(−)-form (FIG. 5+6). Samples of this reactor were analysed by qRT-PCR for expression of the meso-butanediol dehydrogenase gene (see below).

TABLE 6

| media for CSTR operation: | | | |
|---|---|---|---|
| Solution A | | | |
| $NH_4Ac$ | 3.083 g | KCl | 0.15 g |
| $MgCl_2$•$6H_2O$ | 0.4 g | NaCl (optional) | 0.12 g |
| $CaCl_2$•$2H_2O$ | 0.294 g | Distilled Water | Up to 1 L |
| Solution B | | | |
| Biotin | 20.0 mg | Calcium D-(*)-pantothenate | 50.0 mg |
| Folic acid | 20.0 mg | Vitamin B12 | 50.0 mg |
| Pyridoxine•HCl | 10.0 mg | p-Aminobenzoic acid | 50.0 mg |
| Thiamine•HCl | 50.0 mg | Thioctic acid | 50.0 mg |
| Riboflavin | 50.0 mg | Distilled water | To 1 Liter |
| Nicotinic acid | 50.0 mg | | |
| Solution C | | | |
| Component | mmol/L H2O | Component | mmol/L H2O |
| $FeCl_3$ | 0.1 | $Na_2SeO_3$ | 0.01 |
| $CoCl_2$ | 0.05 | $Na_2MoO_4$ | 0.01 |
| $NiCl_2$ | 0.05 | $ZnCl_2$ | 0.01 |
| $H_3BO_3$ | 0.01 | MnCl2 | 0.01 |
| | | Na2WO3 | 0.01 |

Sampling and Analytical Procedures

Media samples were taken from the CSTR reactor at intervals over the course of each fermentation. Each time the media was sampled care was taken to ensure that no gas was allowed to enter into or escape from the reactor.

HPLC:

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 μm. Temperature of column: 60° C. Detector: Refractive Index. Temperature of detector: 45° C.

Method for Sample Preparation:

400 μL of sample and 50 μL of 0.15M ZnSO4 and 50 μL of 0.15M Ba(OH)2 are loaded into an Eppendorf tube. The tubes are centrifuged for 10 min. at 12,000 rpm, 4° C. 200 μL of the supernatant are transferred into an HPLC vial, and 54 are injected into the HPLC instrument.

Headspace Analysis:

Measurements were carried out on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Cell Density:

Cell density was determined by counting bacterial cells in a defined aliquot of fermentation broth. Alternatively, the absorbance of the samples was measured at 600 nm (spectrophotometer) and the dry mass determined via calculation according to published procedures.

Figure 7:
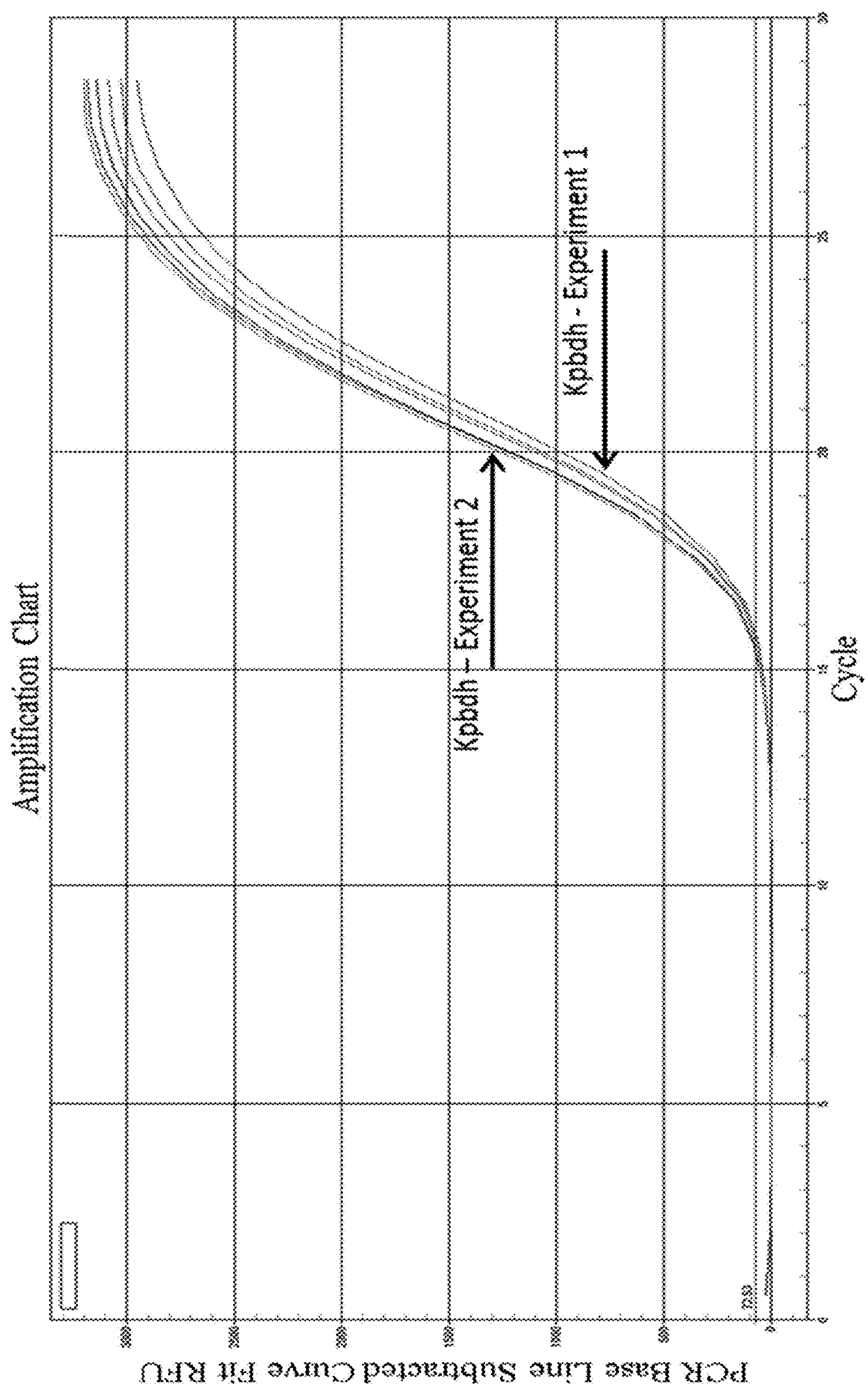
FIG. 7: Amplification chart confirming expression of meso-2,3Butanediol dehydrogenase in *C. autoethanogenum*.

Expression of meso-2,3-butanediol Dehydrogenase budC Gene Expression:

qRT-PCR experiments were performed to confirm successful expression of introduced of meso-2,3-butanediol dehydrogenase budC gene in *C. autoethanogenum* in the growth studies in 12-well plates and continuous fermentation described above. While no amplification was observed with the wild-type strain using oligonucleotide pair KpBDH-F and R, a signal was measured for the strain carrying plasmid pMTL83155-KpBDH for both growth studies at similar level, confirming successful expression of the meso-2,3-butanediol dehydrogenase budC gene (FIG. 7).

1 mL sample of the growth experiment in 12-well-plates (experiment 1) and 4.5 mL sample from a continuous reactor (experiment 2) were taken. Samples were immediately extracted after collection. The culture was centrifuged (5,000×RPM, 10 min, 4° C.). Total RNA was isolated using RiboPure™ (Ambion) according to protocol. Disruption of the cells was carried out using a BeadBeater (Biospec) in three cycles compromising 1 min shake and 1 min ice, elution was performed in 50 μL of RNase/DNase-free water. After DNase I treatment using TURBO™ DNase (Ambion), the reverse transcription step was then carried out using SuperScript III Reverse Transcriptase Kit (Invitrogen, Carlsbad, Calif., USA). RNA was checked using a NanoDrop 2000 (Thermo Scientific). A non-RT control was performed for every oligonucleotide pair. All qRT-PCR reactions were performed in triplicateusing a MyiQ™ Single Colour Detection System (Bio-Rad Labratories, Carlsbad, Calif., USA) in a total reaction volume of 25 μL with 2 ng/μL of cDNA template, 67 nM of each oligonucleotide (Table 7), and 1×iQ™ SYBR® Green Supermix (Bio-Rad Labratories, Carlsbad, Calif., USA). The reaction conditions were 95° C. for 10 min, followed by 40 cycles of 95° C. for 15 s and 72° C. for 1 min. For detection of oligonucleotide dimerisation or other artifacts of amplification, a melting-curve analysis was performed immediately after completion of the qPCR (111 cycles of 40° C. to 95° C. at 0.5° C./s).

TABLE 7

| Oligonucleotides for qRT-PCR | | | |
|---|---|---|---|
| Target | Oligonucleotide Name | DNA Sequence (5' to 3') | SEQ ID NO |
| Guanylate kinase (gnk) | GnK-F | TCAGGACCTTCTGGAAC TGG | 35 |
| | GnK-R | ACCTCCCCTTTTCTTGGA GA | 36 |
| Formate tetrahydrofolate ligase (FoT4L) | FoT4L-F | CAGGTTTCGGTGCTGAC CTA | 37 |
| | FoT4L-F | AACTCCGCCGTTGTATTT CA | 38 |
| meso-2,3-butanediol dehydrogenase budC | KpBDH-F | AAGTTTCTGAGGCTGCA GGT | 39 |
| meso-2,3-butanediol dehydrogenase budC | KpBDH-R | GCTGCAACATCTTCAGG TTCA | 40 |

Production of MEK and 2-butanol from Carbon Monoxide

For production of 2-butanol from CO, meso-23-butanediol dehydrogenase gene budC from *Klebsiella pneumonia* and diol dehydratase genes pddABC from *Klebsiella oxytoca* are introduced simultaneously into carboxydotrophic acetogen like *Clostridium autoethanogenum*. For production of MEK instead of 2-butanol, the alcohol dehydrogenase is knocked-out.

Construction of Expression Vector

Production of MEK or 2-butanol from CO requires a meso-2,3-butanediol producing butanediol dehydrogenase and a diol dehydratase capable of converting the 2,3-butanediol to MEK. For this purpose an expression vector is constructed to express both genes. The codon optimised budC gene from *K. pneumoniae* is cut from pBSK-KpBDH with SalI and XhoI and cloned into the SalI site of pMTL83155-pddABC.

Transformation of *C. autoethanogenum* and Derivative Strains

This vector is used to transform *C. autoethanogenum* and derivative strains with inactivated native dehydrogenases as described above. The various generated strains are then grown on mill gas and tested for the production of the desired metabolite.

Knock-Out of both D-(−)-2,3-butanediol dehydrogenase and Alcohol Dehydrogenase

To eliminate both, production of D-(−)-2,3-Butanediol and conversion of MEK to 2-butanol, both native D-(−)-butanediol dehydrogenase and alcohol dehydrogenase are eliminated.

This can be achieved by two ways (a) homologous recombination and (b) marker less gene disruption using ClosTron tool as explained in Example 1 and Example 3.

(a) Δ2,3bdh ΔSecAdh Double Knockout *C. autoethanogenum* DSM23693 Strain by Homologous Recombination:

The ~1 kb 5' (SEQ ID NO: 16) and 3' (SEQ ID NO: 17) homology arms of 2,3bdh genes are PCR amplified using *C. autoethanogenum* DSM23693 genomic DNA. Primers Og13f (SEQ ID NO: 18)/Og14r (SEQ ID NO: 19) and Og15f (SEQ ID NO: 20)/Og16r (SEQ ID NO: 21) are used to amplify the 5' and 3' homology arms, respectively. The two PCR products are cloned into pMTL85151 plasmids between the Sbf1/Not1 and Nhe1/Asc1 sites to get pMTL85151-2,3bdh-KO. This plasmid is introduced into *C. autoethanogenum* DSM23693 either by conjugation or by electroporation as described in the above examples. Following selection on thiamphenicol plates the transformants are screened for 2,3bdh knockout using the primers Og33f (SEQ ID NO: 22) and Og34r (SEQ ID NO: 23) that flank the homology arms of 2,3bdh for PCR and sequencing of this PCR product.

The plasmid for SecAdh gene knockout can be similarly constructed. The ~1 kb 5' (SEQ ID NO: 24) and 3' (SEQ ID NO: 25) homology arms of 2,3bdh genes are PCR amplified using *C. autoethanogenum* DSM23693 genomic DNA. Primers Sec5f (SEQ ID NO: 26)/Sec5r (SEQ ID NO: 27) and Sec3f (SEQ ID NO: 28)/Sec3r (SEQ ID NO: 29) are used to amplify the 5' and 3' homology arms, respectively. The two PCR products are cloned into pMTL85151 plasmids between the Sbf1/Not1 and Nhe1/Asc1 sites to get pMTL85151-SecAdh-KO. Following selection on thiamphenicol plates the transformants can be screened for SecAdh knockout using the primers SecOSf (SEQ ID NO: 30) and SecO5r (SEQ ID NO: 31) that flank the homology arms of SecAdh gene for PCR.

Once having achieved the knockout of either 2,3bdh or the SecAdh genes in *C. autoethanogenum* DSM23693, the second gene in these single mutants is targeted using either pMTL85151-2,3bdh-KO or pMTL85151-SecAdh-KO plasmids. The plasmid is introduced into the single gene knockout mutant either by electroporation as described above. The transformants can be screened for the knockout of the second gene using the primers flanking the homology arms of the corresponding genes.

(b) Δ2,3bdh ΔSecAdh Double Gene Disruption Using ClosTron:

The RAM ermB cassette in the ClosTron group II intron construct is flanked by Flippase Recombination sites (Frt). By introducing flippase recombinase into Δ2,3bdh ClosTron mutant either by conjugation or by electroporation, the RAM ermB marker of ~1.3 kb can be removed from the genome of the mutant and thus the ermB marker can be recycled. A ~0.8 kb fragment of group II intron will be left on the genome. This can be confirmed by (i) testing its susceptibility to clarithromycin and (ii) by PCR with the primers flanking the group II intron insertion site with the primers Og42f (SEQ ID NO: 12) and Og43r (SEQ ID NO: 13) and sequencing of the PCR product. Once obtaining the Δ2,3bdh ClosTron mutant without RAM ermB marker (Δ2,3bdh-ermB ClosTron), the SecAdh gene in the mutant is targeted in a similar way using ClosTron group II intron insertional inactivation tool. The intron insertion site between bases 399 and 400 has been identified in the SecAdh gene using Perutka algorithm hosted at ClosTron.com and the intron targeting cassette has been designed (SEQ ID NO: 22). The intron targeting cassette is commercially synthesized by DNA2.0 and delivered in pMTL007C-E2 vector as pMTL007C-E5-SecAdh-399!400s which can be introduced into Δ2,3bdh-ermB ClosTron mutant by either conjugation or electroporation. The transformants can be sequentially selected on thiamphenicol and clarithromycin agar plates and screened by PCR with primers SecCTf (SEQ ID NO: 33) and SecCTr (SEQ ID NO: 34) as explained above.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise," "comprising" and the like, are to be construed in an inclusive sense as opposed to an exclusive sense, that is to say, in the sense of "including, but not limited to."

We claim:

1. Genetically engineered, carboxydotrophic, acetogenic bacteria comprising an exogenous nucleic acid encoding a meso-2,3-butanediol dehydrogenase enzyme and an exogenous nucleic acid encoding a diol/glycerol dehydratase enzyme, wherein the bacteria are *Clostridium autoethanogenum* or *Clostridium ljungdahlii.*

2. The bacteria of claim 1, wherein the bacteria comprise a knock-out mutation in one or both of a D-(−)2,3-butanediol dehydrogenase gene and an alcohol dehydrogenase gene.

3. The bacteria of claim 1, wherein the bacteria comprise an exogenous nucleic acid encoding a reactivation protein of the diol/glycerol dehydratase.

4. A nucleic acid encoding a meso-2,3-butanediol dehydrogenase codon-optimized for *Clostridium autoethanogenum*, wherein the nucleic acid comprises SEQ ID NO: 5.

5. A nucleic acid encoding a diol/glycerol dehydratase codon-optimized for *Clostridium autoethanogenum*, wherein the nucleic acid comprises SEQ ID NO: 4.

6. The bacteria of claim 1, wherein the meso-2,3-butanediol dehydrogenase is *Klebsiella pneumoniae* meso-2,3-butanediol dehydrogenase.

7. The bacteria of claim 1, wherein the diol/glycerol dehydratase is *Klebsiella oxytoca* diol/glycerol dehydratase or *Clostridium butyricum* diol/glycerol dehydratase.

8. The bacteria of claim 1, wherein the bacteria are derived from parental bacterium *Clostridium autoethanogenum* deposited under DSMZ Accession No. DSM23693.

9. The bacteria of claim 6, wherein the bacteria comprise a knock-out mutation in one or both of a D-(−)2,3-butanediol dehydrogenase gene and an alcohol dehydrogenase gene.

10. The bacteria of claim 7, wherein the bacteria comprise a knock-out mutation in one or both of a D-(−)2,3-butanediol dehydrogenase gene and an alcohol dehydrogenase gene.

11. The bacteria of claim 6, wherein the bacteria comprise an exogenous nucleic acid encoding a reactivation protein of the diol/glycerol dehydratase.

12. The bacteria of claim 7, wherein the bacteria comprise an exogenous nucleic acid encoding a reactivation protein of the diol/glycerol dehydratase.

13. The bacteria of claim 1, wherein the nucleic acid encoding the meso-2,3-butanediol dehydrogenase comprises SEQ ID NO: 5.

14. The bacteria of claim 1, wherein the nucleic acid encoding the diol/glycerol dehydratase comprises SEQ ID NO: 4.

15. The bacteria of claim 1, wherein the bacteria produce one or both of methyl ethyl ketone and 2-butanol.

* * * * *